(12) United States Patent
Sadeghi et al.

(10) Patent No.: US 9,700,598 B2
(45) Date of Patent: *Jul. 11, 2017

(54) MODIFIED VASOACTIVE INTESTINAL PEPTIDES

(71) Applicant: PhaseBio Pharmaceuticals, Inc., Malvern, PA (US)

(72) Inventors: Homayoun Sadeghi, Hillsborough, NC (US); Suzanne Dagher, Raleigh, NC (US); Andrew Turner, Durham, NC (US)

(73) Assignee: PHASEBIO PHARMACEUTICALS, INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/681,597

(22) Filed: Apr. 8, 2015

(65) Prior Publication Data

US 2016/0220642 A1    Aug. 4, 2016

Related U.S. Application Data

(63) Continuation of application No. 12/857,103, filed on Aug. 16, 2010, now Pat. No. 9,029,505.

(60) Provisional application No. 61/234,151, filed on Aug. 14, 2009.

(51) Int. Cl.
  *A61K 38/22*  (2006.01)
  *A61K 38/39*  (2006.01)

(52) U.S. Cl.
  CPC .......... *A61K 38/2278* (2013.01); *A61K 38/39* (2013.01)

(58) Field of Classification Search
  CPC .......................... A61K 38/2278; A61K 38/39
  See application file for complete search history.

(56) References Cited

U.S. PATENT DOCUMENTS

| | | |
|---|---|---|
| 4,132,746 A | 1/1979 | Urry et al. |
| 4,187,852 A | 2/1980 | Urry et al. |
| 4,474,851 A | 10/1984 | Urry |
| 4,500,700 A | 2/1985 | Urry |
| 4,589,882 A | 5/1986 | Urry |
| 4,605,641 A | 8/1986 | Bolin et al. |
| 4,749,647 A | 6/1988 | Thomas et al. |
| 4,752,638 A | 6/1988 | Nowinski et al. |
| 4,783,523 A | 11/1988 | Urry et al. |
| 4,870,055 A | 9/1989 | Urry et al. |
| 4,898,926 A | 2/1990 | Urry |
| 5,147,855 A | 9/1992 | Gozes et al. |
| 5,234,907 A | 8/1993 | Bolin |
| 5,235,041 A | 8/1993 | Cappello et al. |
| 5,236,904 A | 8/1993 | Gerstenberg et al. |
| 5,243,038 A | 9/1993 | Ferrari et al. |
| 5,288,514 A | 2/1994 | Ellman |
| 5,445,934 A | 8/1995 | Fodor et al. |
| 5,447,912 A | 9/1995 | Gerstenberg et al. |
| 5,496,712 A | 3/1996 | Cappello et al. |
| 5,506,120 A | 4/1996 | Yamamoto et al. |
| 5,514,581 A | 5/1996 | Ferrari et al. |
| 5,519,004 A | 5/1996 | Urry |
| 5,520,672 A | 5/1996 | Urry |
| 5,527,610 A | 6/1996 | Urry |
| 5,545,617 A | 8/1996 | Dartt et al. |
| 5,624,711 A | 4/1997 | Sundberg et al. |
| 5,641,648 A | 6/1997 | Ferrari et al. |
| 5,681,816 A | 10/1997 | Korman |
| 5,702,717 A | 12/1997 | Cha et al. |
| 5,747,646 A | 5/1998 | Hakimi et al. |
| 5,770,570 A | 6/1998 | Paul et al. |
| 5,770,697 A | 6/1998 | Ferrari et al. |
| 5,773,249 A | 6/1998 | Cappello et al. |
| 5,816,259 A | 10/1998 | Rose |
| 5,830,713 A | 11/1998 | Ferrari et al. |
| 5,854,387 A | 12/1998 | Urry et al. |
| 5,900,405 A | 5/1999 | Urry |
| 5,958,881 A | 9/1999 | Korman |
| 5,972,406 A | 10/1999 | Urry et al. |
| 5,972,883 A | 10/1999 | Gozes et al. |
| 5,998,588 A | 12/1999 | Hoffman et al. |
| 6,004,782 A | 12/1999 | Daniell et al. |
| 6,018,030 A | 1/2000 | Ferrari et al. |
| 6,037,321 A | 3/2000 | Cox et al. |
| 6,063,061 A | 5/2000 | Wallace et al. |

(Continued)

FOREIGN PATENT DOCUMENTS

| | | |
|---|---|---|
| JP | 2009-525946 A | 7/2009 |
| WO | WO 96/32406 A1 | 10/1996 |

(Continued)

OTHER PUBLICATIONS

Delgado et al., "The significance of vasoactive intestinal peptide in immunomodulation", Pharmacological Reviews, 56(2): 249-290 (2004).

Domschke et al., "Vasoactive Intestinal Peptide in Man: Pharmacokinetics, Metabolic and Circulatory Effects," Gut, 19: 1049-1053 (1978).

EP Application No. EP 10808864.1, Extended European Search Report dated Feb. 21, 2013.

Gourlet et al., "Vasoactive Intestinal Peptide (VIP) and Pituitary Adenylate Cyclase-Activating Peptide (PACAP-27, but not PACAP-38) Degradation by the Neutral Endopeptidase EC 3.4.24. 11," Biochemical Pharmacology, 54: 509-515 (1997).

(Continued)

*Primary Examiner* — Amber D Steele
(74) *Attorney, Agent, or Firm* — Cooley LLP

(57) ABSTRACT

The present invention provides modified Vasoactive Intestinal Peptides (VIPs), encoding polynucleotides and vectors, as well as pharmaceutical compositions comprising the same. The invention further provides methods of making and using the modified VIP agents. In accordance with the invention the VIP exhibits an extended circulatory half-life, receptor-binding or biological potency, and/or altered receptor binding profile with respect to unmodified VIP.

15 Claims, 18 Drawing Sheets

(56) References Cited

U.S. PATENT DOCUMENTS

| | | |
|---|---|---|
| 6,140,072 A | 10/2000 | Ferrari et al. |
| 6,153,655 A | 11/2000 | Martinez et al. |
| 6,184,348 B1 | 2/2001 | Ferrari et al. |
| 6,200,598 B1 | 3/2001 | Needham |
| 6,258,562 B1 | 7/2001 | Salfield et al. |
| 6,328,996 B1 | 12/2001 | Urry |
| 6,329,209 B1 | 12/2001 | Wagner et al. |
| 6,355,776 B1 | 3/2002 | Ferrari et al. |
| 6,380,154 B1 | 4/2002 | Cappello et al. |
| 6,429,188 B1 | 8/2002 | Perez et al. |
| 6,503,534 B1 | 1/2003 | Pellet et al. |
| 6,537,521 B2 | 3/2003 | Uzgiris |
| 6,541,033 B1 | 4/2003 | Shah |
| 6,582,926 B1 | 6/2003 | Chilkoti |
| 6,593,394 B1 | 7/2003 | Li et al. |
| 6,699,294 B2 | 3/2004 | Urry |
| 6,852,834 B2 | 2/2005 | Chilkoti |
| 6,998,387 B1 | 2/2006 | Goke et al. |
| 7,084,243 B2 | 8/2006 | Glaesner et al. |
| 7,094,755 B2 | 8/2006 | Burman et al. |
| 7,101,843 B2 | 9/2006 | Glaesner et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,176,278 B2 | 2/2007 | Prior |
| 7,226,910 B2 | 6/2007 | Wilson et al. |
| 7,232,879 B2 | 6/2007 | Galloway et al. |
| 7,259,233 B2 | 8/2007 | Dodd et al. |
| 7,271,149 B2 | 9/2007 | Glaesner et al. |
| 7,332,473 B2 | 2/2008 | Onoue et al. |
| 7,364,859 B2 | 4/2008 | Chilkoti |
| 7,429,458 B2 | 9/2008 | Chilkoti |
| 7,442,680 B2 | 10/2008 | Young et al. |
| 7,459,441 B2 | 12/2008 | Minagawa et al. |
| 7,468,353 B2 | 12/2008 | Bevec |
| 7,566,691 B2 | 7/2009 | Nestor |
| 7,582,608 B2 | 9/2009 | Bokvist et al. |
| 7,723,472 B2 | 5/2010 | Szoka et al. |
| 7,776,815 B2 | 8/2010 | Vanderby et al. |
| 8,334,257 B2 | 12/2012 | Chilkoti |
| 9,029,505 B2* | 5/2015 | Sadeghi ............ A61K 38/2278 530/324 |
| 9,458,218 B2 | 10/2016 | Chilkoti |
| 2002/0045567 A1 | 4/2002 | Cappello et al. |
| 2002/0099003 A1 | 7/2002 | Wilson et al. |
| 2002/0151458 A1 | 10/2002 | Gomariz et al. |
| 2003/0059840 A1 | 3/2003 | Chilkoti |
| 2003/0059841 A1 | 3/2003 | Chilkoti |
| 2004/0063631 A1 | 4/2004 | Block |
| 2004/0110296 A1 | 6/2004 | Vargeese et al. |
| 2004/0234609 A1 | 11/2004 | Collier et al. |
| 2005/0118109 A1 | 6/2005 | Block et al. |
| 2005/0203009 A1 | 9/2005 | Pan et al. |
| 2005/0255554 A1 | 11/2005 | Chilkoti |
| 2006/0247156 A1 | 11/2006 | Vanderby et al. |
| 2007/0009602 A1 | 1/2007 | Setton et al. |
| 2008/0085860 A1 | 4/2008 | Bokvist et al. |
| 2008/0108573 A1 | 5/2008 | Duggan |
| 2008/0207492 A1 | 8/2008 | Polt et al. |
| 2008/0221041 A1 | 9/2008 | Block |
| 2008/0261863 A1 | 10/2008 | Whelan et al. |
| 2008/0274961 A1 | 11/2008 | Bevec |
| 2008/0318865 A1 | 12/2008 | Juul-Mortensen |
| 2009/0004104 A1 | 1/2009 | Chilkoti |
| 2009/0005315 A1 | 1/2009 | Duggan |
| 2009/0092582 A1 | 4/2009 | Bogin et al. |
| 2009/0175821 A1 | 7/2009 | Bridon et al. |
| 2009/0270317 A1 | 10/2009 | Chilkoti |
| 2010/0016212 A1 | 1/2010 | Rubin et al. |
| 2010/0022455 A1 | 1/2010 | Chilkoti |
| 2010/0184651 A1 | 7/2010 | Maithal et al. |
| 2010/0256044 A1 | 10/2010 | Roth-chiarello |
| 2011/0039776 A1 | 2/2011 | Chilkoti |
| 2011/0123487 A1 | 5/2011 | Chilkoti |
| 2011/0178017 A1 | 7/2011 | Sadeghi et al. |
| 2014/0073667 A1 | 3/2014 | Morgan |
| 2014/0088141 A1 | 3/2014 | Binch et al. |
| 2014/0364371 A1 | 12/2014 | Setton et al. |
| 2015/0111829 A1 | 4/2015 | Georgopoulos et al. |

FOREIGN PATENT DOCUMENTS

| | | |
|---|---|---|
| WO | WO 2007/057922 A1 | 5/2007 |
| WO | WO 2007/073486 A2 | 6/2007 |
| WO | WO 2008/030968 A2 | 3/2008 |
| WO | WO 2010/080578 A1 | 7/2010 |
| WO | WO 2011/020091 A1 | 2/2011 |
| WO | WO 2012/170524 A1 | 12/2012 |
| WO | WO 2015/172046 A1 | 11/2015 |

OTHER PUBLICATIONS

Izumi et al., "Effect of Amino Terminal Methionine Residue on the Physicochemical Properties and Biological Activity of Recombinant Methionyl Human Interleukin-2 (S-6820)", Basic and Clinical Researches, vol. 24, No. 2, pp. 151-175 (and English Summary) (1990).

Kobayashi et al., "Degradation of Vasoactive Intestinal Polypeptide by Rabbit Gastric Smooth Muscle Membranes," Peptides, 15(2): 323-332 (1994).

Meyer et al., "Polypeptide Fusion Tag for Thermal Purification of Recombinant Proteins," Abstracts of Papers, 217th ACS National Meeting, Anaheim, CA, US, Mar. 21-25, 1999, BIOT-078, see abstract.

Meyer et al., "Drug targeting using thermally responsive polymers and local hyperthermia," Journal of Controlled Release, 74: 213-224 (2001).

Meyer et al., "Targeting a Genetically Engineered Elastin-like Polypeptide to Solid Tumors by Local Hypothermia," Cancer Res., 61(4): 1548-1554 (2001).

Meyer et al. "Purification of Recombinant Proteins by Fusion with Thermally-Responsive Polypeptides", Nature Biotechnology, 17: 1112-1115 (1999).

Meyer et al., "Protein Purification by Fusion with an Environmentally Responsive Elastin-Like Polypeptide: Effect of Polypeptide Length on the Purification of Thioredoxin", Biotechnology Progress, 17: 720-728 (2001).

Onoue et al., "Long-active analague of Vasoactive Intestinal Peptide, [R15, 20, 21, L17]-VIP-GRR (IK212532), Protects Rat Alveolar L2 Cells from the Cytotoxicity of Cigarette Smoke," Regulatory Peptides, 123: 193-199 (2004).

Önyüksel et al., "Human VIP-α: A long-acting, biocompatible and biodegradable peptide nanomedicine for essential hypertension," Peptides, 27: 2271-2275 (2006).

Önyüksel et al., "A Novel Formulation of VIP in Sterically Stabilized Micelles Amplifies Vasodilation In Vivo," Pharmaceutical Research, 16(1): 155-160 (1999).

PCT/US2010/45605, International Search Report mailed Jan. 5, 2011.

PCT/US2010/45605, Written Opinion mailed Jan. 5, 2011.

Pozo et al., "Tuning Immune Tolerance With Vasoactive Intestinal Peptide: A New Therapeutic Approach for Immune Disorders", Peptides, 28(9): 1833-1846 (2007).

Rubinstein et al., "Intratracheal and subcutaneous liposomal VIP normalizes arterial pressure in spontaneously hypertensive hamsters," International Journal of Pharmaceutics, 316: 144-147 (2006).

Sejourne et al., "Development of a Novel Bioactive Formulation of Vasoactive Intestinal Peptide in Sterically Stabilized Liposomes," Pharmaceutical Research, 14(3): 362-365 (1997).

Suzuki et al., "Encapsulation of VIP into liposomes restores vasorelaxation in hypertension in situ," Am. J. Physiol., 271(40): H282-H287 (1996).

Uversky et al., "Structure and stability of recombinant protein depend on the extra N-terminal methionine residue: S6 permutein from direct and fusion expression systems", Biochimica et Biophysica Acta (BBA)—Protein Structure and Molecular Enzymology, 1432(2): 324-332 (1999).

(56) References Cited

OTHER PUBLICATIONS

Yang et al., "Enhanced Inhibition of Human Immunodeficiency Virus Type 1 by Met-Stromal-Derived Factor 1β Correlates with Down-Modulation of CXCR4", Journal of Virology, 73(6): 4582-4589 (1999).
Dvoráková, Magdalena Chottová. "Cardioprotective role of the VIP signaling system." Drug News Perspect (2005); 18(6): 387-391.
Kalfin et al., "Protective role of intracoronary vasoactive intestinal peptide in ischemic and reperfused myocardium." J Pharmacol Exp Ther. (1994); 268(2): 952-958.
Mori et al., "Decreases in substance P and vasoactive intestinal peptide concentrations in plasma of stroke-prone spontaneously hypertensive rats." Japanese Heart Journal (1993); 34(6): 785-794.
Onune et al., "Physicochemical and pharmacological characterization of novel vasoactive intestinal peptide derivatives with improved stability." European Journal of Pharmaceutics and Biopharmaceutics (2009); 73(1): 95-101.
PCT/US2010/45605, International Preliminary Report on Patentability dated Feb. 14, 2012, 7 pages.
Petkov et al., "Vasoactive intestinal peptide as a new drug for treatment of primary pulmonary hypertension." The Journal of Clinical Investigation (2003); 111(9): 1339-1346.
Said et al., "Moderate pulmonary arterial hypertension in male mice lacking the vasoactive intestinal peptide gene." Circulation (2007); 115(10): 1260-1268.
Victor, Z. C., et al. "Vasopeptidase inhibition reverses myocardial vasoactive intestinal peptide depletion and decreases fibrosis in salt sensitive hypertension." European Journal of Pharmacology (2004); 485(1): 235-242.
Ye, V. Z. C., et al. "Myocardial vasoactive intestinal peptide and fibrosis induced by nitric oxide synthase inhibition in the rat." Acta Physiologica Scandinavica (2003); 179(4): 353-360.
Duggan, K.D. et al., "Effects of enalapril on vasoactive intestinal peptide metabolism and tissue levels", European Journal of Pharmacology, 358(1): 25-30 (1998).
EP Application No. EP 12796397.3, Extended European Search Report, dated Dec. 11, 2014, 9 pages.
Free et al. "A Phase 1, Multi-center, Randomized, Double-blind, Placebo Controlled Study to Evaluate the Safety/Tolerability, Pharmacokinetic and Hemodynamic Response Following Single Ascending Subcutaneous Doses of PB 1046 (Vasomera™) in Subjects with Essential Hypertension (Trial Registry No. NCT01523067)," PhaseBio Pharmaceuticals, p. 1, Nov. 2014. Retrieved from the Internet:<http://phasebio.com/wp-content/uploads/2014/12/AHAPresentation-FINAL-V1-12NOV2014.pdf> on Aug. 7, 2015 (Aug. 7, 2015). entire document, 1 page.
Mow et al. "PhaseBio Pharmaceuticals Inc," pp. 1-28, Jun. 2013, entire document. Article Retrieved from the Internet:<http://phasebio.com/wp-content/uploads/2013/12/PhaseBio-Noncon-Jefferies-Presentation-2013.pdf> on Aug. 7, 2015 (Aug. 7, 2015). entire document, 28 pages.
Onoue et al., "Physicochemical and pharmacological characterization of novel vasoactive intestinal peptide derivatives with improved stability." European Journal of Pharmaceutics and Biopharmaceutics (2009); 73(1): 95-101.
PCT/US2012/041092, International Preliminary Report on Patentability, dated Dec. 10, 2013, 5 pages.
PCT/US2012/041092, International Search Report and Written Opinion, dated Sep. 21, 2012, 7 pages.
PCT/US2015/029926, International Preliminary Report on Patentability, dated Nov. 8, 2016, 8 pages.
PCT/US2015/029926, International Search Report and Written Opinion, dated Aug. 25, 2015, 11 pages.
Unverferth et al., "Human and canine ventricular vasoactive intestinal polypeptide: decrease with heart failure." The Journal of Laboratory and Clinical Medicine (1986), 108(1): 11-16.

\* cited by examiner

FIGURE 1

SEQ ID NO. 14

<u>M-VIP ELP1-120</u> (M added to N terminus of VIP)

```
MHSDAVFTDNYTRLRKOMAVKKYLNSILN
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGWP  (SEQ ID NO: 14)
```

ELP1-120 = (VPGXG)$_{120}$ where X = V$_5$G$_3$A$_2$

FIGURE 2

SEQ ID NO. 15

MAA-VIP ELP1-120 (before processing, MAA added to N terminus of VIP)

MAAHSDAVFTDNYTRLRKOMAVKKYLNSILN
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGVG VPGVG VPGGG VPGAG VPGVG VPGVG VPGVG VPGGG VPGAG VPGGG
VPGWP (SEQ ID NO: 15)

ELP1-120 = (VPGXG)$_{120}$ where X = V$_5$G$_3$A$_2$

M.    Mol. wt. markers
1.    PB1046
2.    PB1046 heated*
3.    PB1047
4.    PB1047 heated*
5.    PB1048
6.    PB1048 heated*
M.    Mol. wt. markers

MODIFIED VASOACTIVE INTESTINAL PEPTIDES

CROSS REFERENCE TO RELATED APPLICATIONS

This application is a continuation of U.S. application Ser. No. 12/857,103, filed Aug. 16, 2010, now U.S. Pat. No. 9,029,505, which claims priority under 35 U.S.C. §119(e) to U.S. Provisional Application Ser. No. 61/234,151, filed Aug. 14, 2009, which is herein incorporated by reference in its entirety.

FIELD OF THE INVENTION

The present invention relates to vasoactive intestinal peptides (VIPs) and pharmaceutical compositions comprising the same, including VIPs having an extended circulatory half-life, and VIPs having receptor binding profiles that differ from the unmodified mature peptide.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PHAS_019_02US_SeqList_ST25.txt, date recorded: Apr. 8, 2015, file size 44 kilobytes).

BACKGROUND

Vasoactive intestinal peptide (VIP) has a number of biological effects including with respect to hemostasis, the immune system, and the nervous system. See, Delgado et al., *The Significance of Vasoactive Intestinal Peptide in Immunomodulation*, Pharmacol. Reviews 56 (2):249-290 (2004). For example, VIP has a beneficial effect on blood and pulmonary pressure and on a wide range of immunological and inflammatory conditions. VIP has great potential as an active agent for pulmonary hypertension, chronic obstructive pulmonary disease (COPD), arthritis, inflammatory bowel disease (IBD), and asthma to mention a few.

There are at least two receptors for VIP, including VPAC1 and VPAC2. These receptors bind both VIP and the related molecule pituitary adenylate cyclase-activating polypeptide (PACAP) to some degree. Both receptors are members of the 7-transmembrane G-protein coupled receptor family. VPAC1 is distributed, for example, in the CNS, liver, lung, intestine and T-lymphocytes. VPAC2 is found, for example, in the CNS, pancreas, skeletal muscle, heart, kidney, adipose tissue, testis, and stomach.

The short half-life of VIP renders this peptide impractical as a pharmaceutical agent. See Pozo D, et al., *Tuning immune tolerance with vasoactive intestinal peptide: A new therapeutic approach for immune disorders*. Peptides 28(9): 1833-1846 (2007). Indeed, studies have shown that the half-life of VIP in blood is less than 2 minutes (Domschke et al., 1978, Gut 19: 1049-53; Burhol et al., 1978, *Scand J Gastroent* 13: 807-813). Further, the multitude of biological effects of VIP may complicate its development for any particular indication. Modified versions of VIP are therefore needed to render the agent therapeutically practical, for example, by extending half-life and/or designing molecules having desirable receptor-binding profiles.

SUMMARY OF THE INVENTION

The present invention provides modified Vasoactive Intestinal Peptides (VIPs), as well as encoding polynucleotides and vectors, and pharmaceutical compositions comprising the modified VIPs. The invention further provides methods of making the modified VIP molecules, and methods of using the modified VIP agents for the treatment of patients. In accordance with the invention, the modified VIP exhibits an extended circulatory half-life or persistence in the body, and/or comparable receptor-binding and/or biological potency, and/or altered receptor binding profile with respect to unmodified VIP.

In one aspect, the invention provides modified VIP molecules and pharmaceutical compositions comprising the same. The modified VIP molecules are recombinantly or chemically modified at the N- and/or C-termini by addition of one or more amino acids, and/or by fusion to heterologous amino acid sequences, so as to provide a longer circulatory half-life or persistence in the body, comparable biological potency, and/or a modified receptor binding profile. For example, in some embodiments, the 28-amino acid mature VIP, which begins with an N-terminal His, comprises additional N-terminal amino acids, such as a single amino acid at the N-terminus (e.g., Met). In these or other embodiments, the modified VIP contains an N- or C-terminal fusion to an Elastin-Like-Peptide (ELP) as described herein. Such modified VIP molecules may show an increased circulatory half-life or persistence in the body, and/or an altered binding preference for VPAC2 over VPAC1.

For example, a VIP may be fused (e.g., by recombinant means) to the N-terminus of an ELP. The histidine of the natural, mature VIP may be at the N-terminus. Such therapeutic agents may require significantly less frequent dosing than the unfused counterpart, such as dosing of from about 1-7 times per week (e.g. daily or weekly dosing).

In alternative embodiments, the VIP-ELP fusion may contain a methionine at the N-terminus with the His of the natural mature VIP product at position 2. In yet other embodiments, the VIP-ELP molecule starts with methionine alanine alanine. When produced in bacteria, the first methionine is lost and the product contains Ala-Ala at the N-terminus. Ala-Ala is removed in vitro or in vivo by the action of DPP-IV peptidase, thereby leaving the natural mature VIP N-terminus. These constructs containing additional amino acids at the N-terminus exhibit a significantly different activity when tested for binding activity at VPAC1 and VPAC2 receptors. For example, while both constructs can activate the VPAC2 receptor with a similar EC50, a construct with methionine at the N-terminus (and His at position 2) is at least 100 fold less active at the VPAC1 receptor.

In various embodiments, the modified VIP of the invention having an N-terminal Met has the advantage of being obtainable by recombinant means, such as by production in *E. coli* or other expression system, without further post-expression manufacturing processes to expose the natural or desired VIP N-terminus.

In still other embodiments, VIP may be chemically modified, for example, by the addition of one or more PEG or other chemical moieties (e.g., at or near the N-terminus), as described in detail herein.

In other aspects, the present invention provides polynucleotides and vectors encoding the modified VIP of the invention, as well as host cells containing the same. The host cells may be suitable for recombinant production of the modified VIP, such as bacterial or yeast cells suitable for use with known expression systems.

In other aspects, the invention provides methods of treating, ameliorating, or preventing a condition in a mammal. Such conditions include a variety of cardiovascular, immunological (e.g., autoimmune), and neurological conditions.

For example, the modified VIP may be used to adjust the balance between pro-inflammatory and anti-inflammatory effectors in a patient, including a patient suffering from an autoimmune disease or inflammatory condition. Exemplary indications for the modified VIP include hypertension, chronic obstructive pulmonary disease (COPD), diabetes, myocardial fibrosis, heart failure, cardiomyopathy, arthritis, inflammatory bowel disease (IBD), and asthma, among others.

DESCRIPTION OF THE FIGURES

FIG. 1 shows the amino acid sequence of a modified VIP-ELP fusion protein (M-VIP-ELP1-120, SEQ ID NO: 14) having Met at the N-terminus and 120 ELP1 units (VPGXG, SEQ ID NO: 3) fused to the VIP at the C-terminus.

FIG. 2 shows the amino acid sequence of a modified VIP-ELP fusion protein (MAA-VIP-ELP1-120, SEQ ID NO: 15) having Met-Ala-Ala at the N-terminus, which is activatable to the natural mature VIP peptide, and 120 ELP1 units (VPGXG, SEQ ID NO: 3) fused to the VIP at the C-terminus.

DETAILED DESCRIPTION OF THE INVENTION

Figure 3:
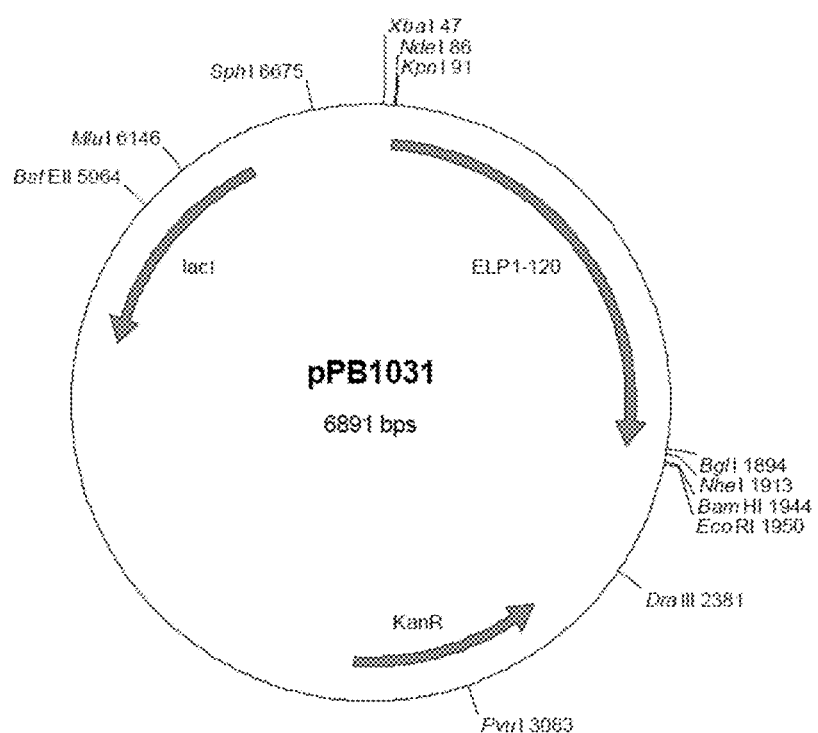
FIG. 3 is a plasmid map of pPB1031, which encodes ELP1-120 for convenient production of recombinant fusions.

The present invention provides modified Vasoactive Intestinal Peptides (VIPs), encoding polynucleotides and vectors, as well as pharmaceutical compositions comprising the modified VIPs. The invention further provides methods of making and using the modified VIP agents for the treatment of patients. In accordance with the invention the VIP may exhibit an extended circulatory half-life or persistence in the body, comparable receptor-binding or biological potency, and/or altered receptor binding profile with respect to unmodified VIP. In various embodiments, the compounds of the invention exhibit a reduced dosing frequency as compared to unmodified counterparts.

Vasoactive Intestinal Peptide

Vasoactive intestinal peptide (VIP) is a peptide hormone containing 28 amino acid residues and is produced in many areas of the human body including the gut, pancreas and suprachiasmatic nuclei of the hypothalamus in the brain. VIP exhibits a wide variety of biological actions including systemic vasodilation, hypotension, increased cardiac output, respiratory stimulation, hyperglycemia, coronary dilation, bronchodilation in animals and humans. VIP also affects the balance of the immune system.

VIP has an effect on several parts of the body. With respect to the digestive system, VIP may induce smooth muscle relaxation (lower esophageal sphincter, stomach, gallbladder), stimulate secretion of water into pancreatic juice and bile, and cause inhibition of gastric acid secretion and absorption from the intestinal lumen. Its role in the intestine is to stimulate secretion of water and electrolytes, as well as dilating intestinal smooth muscle, dilating peripheral blood vessels, stimulating pancreatic bicarbonate secretion, and inhibiting gastrin-stimulated gastric acid secretion. These effects work together to increase motility. VIP has the function of stimulating pepsinogen secretion by chief cells.

VIP has been found in the heart and has significant effects on the cardiovascular system. It causes coronary vasodilation, as well as having a positive inotropic and chronotropic effect.

VIP is an immunomodulating peptide useful for treating inflammation and TH1-type autoimmune disease (See Delgado et al., *The Significance of Vasoactive Intestinal Peptide in Immunomodulation, Pharmacol. Reviews* 56(2):249-290 (2004)). VIP is useful for the treatment of neurodegenerative diseases (see U.S. Pat. No. 5,972,883, which is hereby incorporated by reference in its entirety). VIP and its structurally related peptide pituitary adenylate cyclase-activating polypeptide (PACAP) have important therapeutic effects in chronic inflammatory rheumatic disease, such as osteoarthritis (OA) and rheumatoid arthritis (RA) by down-regulating both the inflammatory and autoimmune components of the disease (Juarranz et al., *Vasoactive intestinal peptide modulates proinflammatory mediator synthesis in osteoarthritic and rheumatoid synovial cells, Rheumatology,* 2004, 43:416-422). In addition, VIP participates in maintaining immune tolerance by regulating the balance between proinflammatory and anti-inflammatory effectors, or by inducing the emergence of T-cells having a suppressor activity against auto-reactive T-cells (Pozo et al., *Tuning immune tolerance with vasoactive intestinal peptide: A new therapeutic approach for immune disorders, Peptide,* 2007, 28(9):1833-1846).

Mature VIP has 28 amino acid residues with the following sequence: HSDAVFTDNYTRLRKQMAVKKYLNSILN (SEQ ID NO: 13). VIP results from processing of the 170-amino acid precursor molecule prepro-VIP. Structures of VIP and exemplary analogs have been described in U.S. Pat. Nos. 4,835,252, 4,939,224, 5,141,924, 4,734,400, 4,605,641, 6,080,837, 6,316,593, 5,677,419, 5,972,883, 6,489,297, 7,094,755, and 6,608,174, each of which is hereby incorporated by reference in its entirety for all purposes.

A number of mutations to improve peptide stability against proteases etc. are detailed in the literature (see Onune et al *Physicochemical and pharmacological characterization of novel vasoactive intestinal peptide derivatives with improved stability, Eur. J. Pharm. Biopharm.* 2009, which is hereby incorporated by reference in its entirety for all purposes). These modified VIP peptides have sequences of SEQ ID NO. 21 (M17L, to prevent oxidation of Met), SEQ ID NO. 22 (K15R, K20R and K21R, to increase proteolytic stability), and SEQ ID NO. 23 (N24A and S25A, to increase proteolytic/thermal stability). The present invention provides modified VIP peptides that include one or more of these modifications, and with additional VIP modifications described herein. Examples of modified VIP molecules include the modified VIP peptides of SEQ ID NOs. 14-15, 17-27, 40, 42, 44, and 50.

In various embodiments described herein, a modified VIP (e.g., comprising SEQ ID NO: 13) (or a functional analog as described herein) is provided. Generally, functional analogs of VIP, include functional fragments truncated at the N- or C-terminus by from 1 to 10 amino acids, including by 1, 2, 3, or up to about 5 amino acids (with respect to SEQ ID NO: 13). Such functional analogs may contain from 1 to 5 amino acid insertions, deletions, and/or substitutions (collectively) with respect to the native sequence (e.g., SEQ ID NO: 13), and in each case retaining the activity of the peptide (e.g., through VPAC2 and/or VPAC1 binding). Such activity may be confirmed or assayed using any available assay, including an assay described herein, and including any suitable assay to determine or quantify an activity described in Delgado et al., *The Significance of Vasoactive Intestinal Peptide in Immunomodulation, Pharmacol. Reviews* 56(2):249-290 (2004). In these or other embodiments, the VIP component of the modified VIP of the invention has at least about 50%, 75%, 80%, 85%, 90%, 95%, or 97% identity with the native mature sequence (SEQ ID NO: 13). The determination of sequence identity between two sequences (e.g., between a native sequence and a functional analog) can be accomplished using any alignment tool, including Tatusova et al., *Blast 2 sequences—a new tool for comparing protein and nucleotide sequences, FEMS Microbiol Lett.* 174:247-250 (1999).

In one aspect, the present invention provides a modified VIP molecule having receptor preference for VPAC2 or VPAC1, as compared to unmodified VIP (e.g., a peptide consisting of the amino acid sequence of SEQ ID NO: 13). For example, the modified VIP may have a relative binding preference for VPAC2 over VPAC1 of at least about 2:1, about 5:1, about 10:1, about 25:1, about 50:1, about 100:1, about 500:1 or more. In other embodiments, the modified VIP may have a relative binding preference for VPAC1 over VPAC2 of at least about 2:1, about 5:1, about 10:1, about 25:1, about 50:1, about 100:1, about 500:1, or more. For example, in certain embodiments, the modified VIP activates the VPAC2 receptor substantially as mature, unmodified, human VIP, that is, with an EC50 within a factor of about 2 of mature, unmodified, human VIP (SEQ ID NO: 13). However, this same modified VIP is 50- or 100-fold or more less effective than mature, unmodified, human VIP in activating the VPAC1 receptor.

Such modified VIP molecules may contain modified N-terminal regions, such as an addition of from 1 to about 500 amino acids to the N-terminal histidine of VIP, which may include heterologous mammalian amino acid sequence. For example, the modified VIP may contain a single methionine at the N-terminal side of the natural N-terminal histidine of mature VIP. This molecule is also conveniently prepared in *E. coli* or other bacterial expression system, since the methionine will not be removed by *E coli* when the adjacent amino acid is histidine. Alternatively, the N-terminal amino acid may be any of the naturally-occurring amino acids, namely alanine, arginine, asparagine, aspartic acid, cysteine, glutamic acid, glutamine, glycine, histidine, isoleucine, leucine, lysine, methionine, phenylalanine, serine, threonine, tryptophan, tyrosine, valine, and proline.

The additional sequence added to the N-terminus of VIP may be of any sequence, including biologically active and biologically inert sequences of from 1 to about 100, 1 to about 50, 1 to about 20, 1 to about 10, and 1 to about 5 amino acids.

The N-terminus of the modified VIP may have the structure M-N, where M is methionine, and N is the N-terminus of the VIP molecule (e.g., SEQ ID No. 14, FIG. 1). This methionine supports translation of the protein in a bacterial or eukaryotic host cell. Thus, the modified VIP can be made in a biological system, including bacterial and yeast expression systems (e.g., *E. coli*). While methionine can sometimes be removed by methionine aminopeptidase (MA) in bacterial expression systems, histidine (H) is one of the least favored residues at position 2 for MA.

In still other embodiments, the N-terminus is modified by fusion with a mammalian heterologous protein, such as a mammalian protein effective for extending half-life of therapeutic molecules. Such sequences may be mammalian sequences, such as albumin, transferrin, or antibody Fc sequences. Such sequences are described in See U.S. Pat. No. 7,238,667 (particularly with respect to albumin conjugates), U.S. Pat. No. 7,176,278 (particularly with respect to transferrin conjugates), and U.S. Pat. No. 5,766,883, which are each hereby incorporated by reference in their entireties.

In other embodiments, the VIP is activatable by a peptidase or protease, such as an endogenous peptidase or protease. Such activatable sequences are described in International Application No. PCT/US2009/068656, which is hereby incorporated by reference in its entirety. As used herein, the terms "peptidase" and "protease" are interchangeable. For example, the VIP may be designed to be activatable by a dipeptidyl peptidase. Exemplary dipeptidyl peptidases include dipeptidyl peptidase-1 (DPP-I), dipeptidyl peptidase-3 (DPP-III), dipeptidyl peptidase-4 (DPP-IV), dipeptidyl peptidase-6 (DPP-VI), dipeptidyl peptidase-7 (DPP-VII), dipeptidyl peptidase-8 (DPP-VIII), dipeptidyl peptidase-9 (DPP-IX), dipeptidyl peptidase-10 (DPP-X). Substrate sequences for such dipeptidases are known.

The N-terminus of an activatable VIP may have the structure Z—N, where Z is a substrate for a dipeptidase (e.g., Z is removed by dipeptidase exposure), and N is the N-terminus of VIP. The activatable VIP may have an N-terminal sequence with the formula M-X—N where M is methionine, X is Pro, Ala, or Ser, and N is the N-terminal of VIP or VIP analog. In this manner, M and X will be sensitive to, and removed by a host cell (e.g., *E. coli.*), and/or a dipeptidase (e.g., DPP-IV), subsequently. Alternatively, the N-terminal sequence of the activatable VIP may be X1-X2-N, where X1 is Gly, Ala, Ser, Cys, Thr, Val, or Pro; X2 is Pro, Ala, or Ser; and N is the N-terminal of VIP. X1-X2 is a substrate for dipeptidase (e.g., DPP-IV), and dipeptidase digestion will expose N, the desired N-terminus of the VIP or the VIP analog (e.g., SEQ ID NO. 15, FIG. 2). In such embodiments, the protein may be produced by expression of a construct encoding M-X1-X2-N (where M is methionine) in a host cell (e.g., *E. coli.*), since Gly, Ala, Ser, Cys, Thr, Val, or Pro at the second position will signal the removal of the Met, thereby leaving X1-X2 on the N-terminus, which can be activated by a dipeptidase (e.g., DPP-IV) in vivo. Such activatable VIP molecules, which are activated to possess the natural mature VIP N-terminus, do not show receptor preference.

In another embodiment, the N-terminus of the modified activatable VIP may have the structure M-Z—N, where M is methionine, Z is a substrate for a dipeptidase (e.g., Z is removed by dipeptidase exposure), and N is a non-His N-terminal of an active VIP (modified VIP). For example, the modified activatable VIP may have an N-terminal sequence with the formula M-X—N where M is methionine; X is Pro, Ala, or Ser; and N is a non-His N-terminal of the active VIP. In this manner, M and X will be sensitive to, and removed by a host cell (e.g., *E. coli.*), and/or a dipeptidase (e.g., DPP-IV), subsequently. Alternatively, the N-terminal sequence of the activatable VIP may be X1-X2-N, where X1 is Gly, Ala, Ser, Cys, Thr, Val, or Pro; X2 is Pro, Ala, or Ser; and N is a non-His N-terminal of the active VIP. X1-X2 is a substrate for dipeptidase (e.g., DPP-IV), and dipeptidase digestion will expose N, the desired non-His N-terminus of the VIP.

Still in another embodiment, the N-terminus of a modified activatable VIP may have the structure M-Z—S—N, where M is methionine; Z is a substrate for a dipeptidase (e.g., Z is removed by dipeptidase exposure); N is the N-terminus of mature VIP (His); and S is one or more amino acids which will be exposed after dipeptidase digestion, and which provide a modified VIP as previously described. For example, the modified activatable VIP may have an N-terminal sequence with the formula M-X—S—N where M is methionine, X is Pro, Ala, or Ser; N is the N-terminal of mature VIP; and S is one or more amino acids which will be exposed after dipeptidase digestion, and will provide receptor preference. Alternatively, the N-terminal sequence of the activatable VIP may be X1-X2-S—N, where X1 is Gly, Ala, Ser, Cys, Thr, Val, or Pro; X2 is Pro, Ala, or Ser; N is a non-His N-terminal of VIP; and S is one or more amino acids which will be exposed after dipeptidase digestion. X1-X2 is a substrate for dipeptidase (e.g., DPP-IV), and dipeptidase digestion will expose S.

In these or other embodiments, N-terminal chemical modifications to the VIP N-terminus may provide receptor preference. Chemical modification of proteins and methods thereof are well known in the art. Non-limiting exemplary chemical modifications are PEGylation, methylglyoxalation, reductive alkylation, performic acid oxidation, succinylation, aminoethylation, and lipidation (Clifton, New Protein Techniques, New Jersey: Humana Press, 1985. ISBX. 0-89603-126-8. Volume. 3 of. Methods in Molecular Biology). Chemical groups, such as PEGylation, may be attached by modifications of cysteine, methionine, histidine, lysine, arginine, tryptophan, tyrosine, carboxyl groups have been described previously (see Lundblad, Techniques in Protein Modification, CRC Press, 1995).

Fusions to Bioelastic Polymers

In some embodiments, the VIP of the invention contains an N-terminal and/or C-terminal bioelastic polymer component. A "bioelastic polymer" may exhibit an inverse temperature transition. Bioelastic polymers are known and described in, for example, U.S. Pat. No. 5,520,672 to Urry et al. Bioelastic polymers may be polypeptides comprising elastomeric units of pentapeptides, tetrapeptides, and/or nonapeptides (e.g. "elastin-like peptides"). Bioelastic polymers that may be used to carry out the present invention are set forth in U.S. Pat. No. 4,474,851, which describes a number of tetrapeptide and pentapeptide repeating units that can be used to form a bioelastic polymer. Specific bioelastic polymers are also described in U.S. Pat. Nos. 4,132,746; 4,187,852; 4,500,700; 4,589,882; and 4,870,055. Still other examples of bioelastic polymers are set forth in U.S. Pat. No. 6,699,294, U.S. Pat. No. 6,753,311, and U.S. Pat. No. 6,063,061. The structures of such bioelastic polymers are hereby incorporated by reference.

In one embodiment, the bioelastic polymers are polypeptides of the general formula (VPGXG)$_m$ where X is any amino acid (e.g., Ala, Leu, Phe) and m is from about 20 to about 2000, or about 50 to about 180. In exemplary embodiments, m is 60, 90, 120, 150, or 180. The frequency of the various amino acids as the fourth amino acid can be changed, as well as the identity of X.

For example, bioelastic polymers may comprise repeating elastomeric units selected from bioelastic pentapeptides and tetrapeptides, where the repeating units comprise amino acid residues selected from the group consisting of hydrophobic amino acid and glycine residues and where the repeating units exist in a conformation having a beta-turn of the formula:

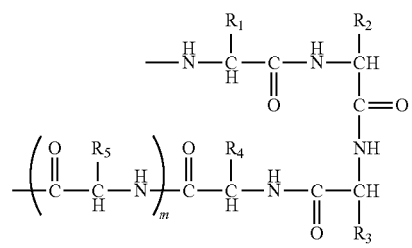

wherein $R_1$-$R_5$ represent side chains of amino acid residues 1-5, and m is 0 when the repeating unit is a tetrapeptide or 1 when the repeating unit is a pentapeptide. Nonapeptide repeating units generally consist of sequential tetra- and pentapeptides. Hydrophobic amino acid residues are selected from alanine, valine, leucine, isoleucine, proline, phenylalanine, tryptophan, and methionine. In many cases, the first amino acid residue of the repeating unit is a residue of valine, leucine, isoleucine or phenylalanine; the second amino acid residue is a residue of proline; the third amino acid residue is a residue of glycine; and the fourth amino acid residue is glycine or a very hydrophobic residue such as tryptophan, phenylalanine or tyrosine. Particular examples include the tetrapeptide Val-Pro-Gly-Gly, the tetrapeptide GGVP, the tetrapeptide GGFP, the tetrapeptide GGAP, the pentapeptide is Val-Pro-Gly-Val-Gly, the pentapeptide GVGVP, the pentapeptide GKGVP, the pentapeptide GVGFP, the pentapeptide GFGFP, the pentapeptide GEGVP, the pentapeptide GFGVP, and the pentapeptide GVGIP. See, e.g., U.S. Pat. No. 6,699,294.

In certain exemplary embodiments, the VIP of the invention contains an N-terminal and/or C-terminal ELP component. The ELP component comprises or consists of structural peptide units or sequences that are related to, or derived from, the elastin protein. Such sequences are useful for improving the properties of therapeutic proteins in one or more of bioavailability, therapeutically effective dose and/or administration frequency, biological action, formulation compatibility, resistance to proteolysis, solubility, half-life or other measure of persistence in the body subsequent to administration, and/or rate of clearance from the body. See, for example, WO 2008/030968 which is hereby incorporated by reference in its entirety.

When the ELP is positioned at the C-terminus of VIP, additional modifications may be made at the VIP N-terminus, such as the addition of one or more amino acids, as described above. In alternative embodiments, there are no such modifications at the VIP N-terminus.

The ELP component is constructed from structural units of from three to about twenty amino acids, or in some embodiments, from four to ten amino acids, such as five or six amino acids. The length of the individual structural units, in a particular ELP component, may vary or may be uniform. In certain embodiments, the ELP component is constructed of a polytetra-, polypenta-, polyhexa-, polyhepta-, polyocta-, and polynonapeptide motif of repeating structural units. Exemplary structural units include units defined by SEQ ID NOs: 1-12 (see below), which may be employed as repeating structural units, including tandem-repeating units, or may be employed in some combination, to create an ELP effective for improving the properties of the therapeutic component. Thus, the ELP component may comprise or consist essentially of structural unit(s) selected from SEQ ID NOS: 1-12, as defined below.

The ELP component, comprising such structural units, may be of varying sizes. For example, the ELP component may comprise or consist essentially of from about 10 to about 500 structural units, or in certain embodiments about 20 to about 200 structural units, or in certain embodiments from about 50 to about 150 structural units, or from about 75 to about 130 structural units, including one or a combination of units defined by SEQ ID NOS: 1-12. The ELP component may comprise about 120 structural units, such as repeats of structural units defined by SEQ ID NO: 3 (defined below). Thus, the ELP component may have a length of from about 50 to about 2000 amino acid residues, or from about 100 to about 600 amino acid residues, or from about 200 to about 500 amino acid residues, or from about 200 to about 400 amino acid residues.

In some embodiments, the ELP component, or in some cases the therapeutic agent, has a size of less than about 150 kDa, or less than about 100 kDa, or less than about 55 kDa, or less than about 50 kDa, or less than about 40 kDa, or less than about 30 or 25 kDa.

In some embodiments, the ELP component in the untransitioned state may have an extended, relatively unstructured and non-globular form so as to escape kidney filtration. In such embodiments, the therapeutic agents of the invention have a molecular weight of less than the generally recognized cut-off for filtration through the kidney, such as less than about 60 kD, or in some embodiments less than about 55, 50, 45, 40, 30, or 25 kDa, and nevertheless persist in the body by at least 2-fold, 3-fold, 4-fold, 5-fold, 10-fold, 20-fold, or 100-fold longer than an uncoupled (e.g., unfused or unconjugated) therapeutic counterpart.

In these or other embodiments, the ELP component does not substantially or significantly impact the biological action of the therapeutic peptide. Thus, the VIP with ELP fusion of the present invention may exhibit a potency (biological action) that is the same or similar to its unfused counterpart. The VIP with ELP fusion of the present invention may exhibit a potency or level of biological action (e.g., as tested in vitro or in vivo) of from 10-100% of that exhibited by the unfused counterpart in the same assay. In various embodiments, the (activated) VIP with ELP fusion of the present invention may exhibit a potency or level of biological action (e.g., as tested in vitro or in vivo) of at least 50%, 60%, 75%, 80%, 90%, 95% or more of that exhibited by the unfused counterpart.

In certain embodiments, the ELP component undergoes a reversible inverse phase transition. That is, the ELP components are structurally disordered and highly soluble in water below a transition temperature (Tt), but exhibit a sharp (2-3° C. range) disorder-to-order phase transition when the temperature is raised above the Tt, leading to desolvation and aggregation of the ELP components. For example, the ELP forms insoluble polymers, when reaching sufficient size, which can be readily removed and isolated from solution by centrifugation. Such phase transition is reversible, and isolated insoluble ELPs can be completely resolubilized in buffer solution when the temperature is returned below the Tt of the ELPs. Thus, the therapeutic agents of the invention can, in some embodiments, be separated from other contaminating proteins to high purity using inverse transition cycling procedures, e.g., utilizing the temperature-dependent solubility of the therapeutic agent, or salt addition to the medium. Successive inverse phase transition cycles can be used to obtain a high degree of purity. In addition to temperature and ionic strength, other environmental variables useful for modulating the inverse transition of the therapeutic agents include pH, the addition of inorganic and organic solutes and solvents, side-chain ionization or chemical modification, and pressure.

In certain embodiments, the ELP component does not undergo a reversible inverse phase transition, or does not undergo such a transition at a biologically relevant Tt, and thus the improvements in the biological and/or physiological properties of the molecule (as described elsewhere herein), may be entirely or substantially independent of any phase transition properties. Nevertheless, such phase transition properties may impart additional practical advantages, for example, in relation to the recovery and purification of such molecules.

In the practice of the present invention, the ELP component functions to stabilize or otherwise improve the VIP component in the therapeutic composition. Subsequent to administration of the coupled VIP-ELP construct to the patient in need of the VIP therapeutic agent, the VIP component and the ELP remain coupled with one another while the VIP is therapeutically active, e.g., for treatment or prophylaxis of a disease state or physiological condition, or other therapeutic intervention.

In certain embodiments, the ELP component(s) may be formed of structural units, including but not limited to:
  (a) the tetrapeptide Val-Pro-Gly-Gly, or VPGG (SEQ ID NO: 1);
  (b) the tetrapeptide Ile-Pro-Gly-Gly, or IPGG (SEQ ID NO: 2);
  (c) the pentapeptide Val-Pro-Gly-X-Gly (SEQ ID NO: 3), or VPGXG, where X is any natural or non-natural amino acid residue, and where X optionally varies among polymeric or oligomeric repeats;

(d) the pentapeptide Ala-Val-Gly-Val-Pro, or AVGVP (SEQ ID NO: 4);

(e) the pentapeptide Ile-Pro-Gly-X-Gly, or IPGXG (SEQ ID NO: 5), where X is any natural or non-natural amino acid residue, and where X optionally varies among polymeric or oligomeric repeats;

(e) the pentapeptide Ile-Pro-Gly-Val-Gly, or IPGVG (SEQ ID NO: 6);

(f) the pentapeptide Leu-Pro-Gly-X-Gly, or LPGXG (SEQ ID NO: 7), where X is any natural or non-natural amino acid residue, and where X optionally varies among polymeric or oligomeric repeats;

(g) the pentapeptide Leu-Pro-Gly-Val-Gly, or LPGVG (SEQ ID NO: 8);

(h) the hexapeptide Val-Ala-Pro-Gly-Val-Gly, or VAPGVG (SEQ ID NO: 9);

(I) the octapeptide Gly-Val-Gly-Val-Pro-Gly-Val-Gly, or GVGVPGVG (SEQ ID NO: 10);

(J) the nonapeptide Val-Pro-Gly-Phe-Gly-Val-Gly-Ala-Gly, or VPGFGVGAG (SEQ ID NO: 11); and (K) the nonapeptides Val-Pro-Gly-Val-Gly-Val-Pro-Gly-Gly, or VPGVGVPGG (SEQ ID NO: 12).

Such structural units defined by SEQ ID NOS:1-12 may form structural repeat units, or may be used in combination to form an ELP component in accordance with the invention. In some embodiments, the ELP component is formed entirely (or almost entirely) of one or a combination of (e.g., 2, 3 or 4) structural units selected from SEQ ID NOS: 1-12. In other embodiments, at least 75%, or at least 80%, or at least 90% of the ELP component is formed from one or a combination of structural units selected from SEQ ID NOS: 1-12, and which may be present as repeating units.

In certain embodiments, the ELP component(s) contain repeat units, including tandem repeating units, of the pentapeptide Val-Pro-Gly-X-Gly (SEQ ID NO: 3), where X is as defined above, and where the percentage of Val-Pro-Gly-X-Gly (SEQ ID NO: 3) pentapeptide units taken with respect to the entire ELP component (which may comprise structural units other than VPGXG (SEQ ID NO: 3)) is greater than about 75%, or greater than about 85%, or greater than about 95% of the ELP component. The ELP component may contain motifs having a 5 to 15-unit repeat (e.g. about 10-unit or about 12-unit repeat) of the pentapeptide of SEQ ID NO: 3, with the guest residue X varying among at least 2 or at least 3 of the structural units within each repeat. The guest residues may be independently selected, such as from the amino acids V, I, L, A, G, and W (and may be selected so as to retain a desired inverse phase transition property). Exemplary motifs include VPGXG (SEQ ID NO: 3), where the guest residues are V (which may be present in from 40% to 60% of structural units), G (which may be present in 20% to 40% of structural units, and A (which may be present in 10% to 30% of structural units). The repeat motif itself may be repeated, for example, from about 5 to about 20 times, such as about 8 to 15 times (e.g., about 12 times), to create an exemplary ELP component. The ELP component as described in this paragraph may of course be constructed from any one of the structural units defined by SEQ ID NOS: 1-12, or a combination thereof. An exemplary ELP component is shown in FIG. 1 fused to the C-terminus of VIP.

In some embodiments, the ELP units may form a β-turn structure that provides an elastin-like property (e.g., inverse phase transition). Exemplary peptide sequences suitable for creating a 3-turn structure are described in International Patent Application PCT/US96/05186, which is hereby incorporated by reference in its entirety. For example, the fourth residue (X) in the elastin pentapeptide sequence, VPGXG (SEQ ID NO: 3), can be altered without eliminating the formation of a 3-turn.

In certain embodiments, the ELP components include polymeric or oligomeric repeats of the pentapeptide VPGXG (SEQ ID NO: 3), where the guest residue X is any amino acid. X may be a naturally occurring or non-naturally occurring amino acid. In some embodiments, X is selected from alanine, arginine, asparagine, aspartic acid, cysteine, glutamic acid, glutamine, glycine, histidine, isoleucine, leucine, lysine, methionine, phenylalanine, serine, threonine, tryptophan, tyrosine and valine. In some embodiments, X is a natural amino acid other than proline or cysteine.

The guest residue X (e.g., with respect to SEQ ID NO: 3, or other ELP structural unit) may be a non-classical (non-genetically encoded) amino acid. Examples of non-classical amino acids include: D-isomers of the common amino acids, 2,4-diaminobutyric acid, α-amino isobutyric acid, A-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general.

Selection of X may be independent in each ELP structural unit (e.g., for each structural unit defined herein having a guest residue X). For example, X may be independently selected for each structural unit as an amino acid having a positively charged side chain, an amino acid having a negatively charged side chain, or an amino acid having a neutral side chain, including in some embodiments, a hydrophobic side chain.

In still other embodiments, the ELP component(s) may include polymeric or oligomeric repeats of the pentapeptides VPGXG (SEQ ID NO:3), IPGXG (SEQ ID NO:5) or LPGXG (SEQ ID NO:7), or a combination thereof, where X is as defined above.

In each embodiment, the structural units, or in some cases polymeric or oligomeric repeats, of the ELP sequences may be separated by one or more amino acid residues that do not eliminate the overall effect of the molecule, that is, in imparting certain improvements to the therapeutic component as described. In certain embodiments, such one or more amino acids also do not eliminate or substantially affect the phase transition properties of the ELP component (relative to the deletion of such one or more amino acids).

The structure of the resulting ELP components may be described using the notation ELPk [$X_iY_j$-n], where k designates a particular ELP repeat unit, the bracketed capital letters are single letter amino acid codes and their corresponding subscripts designate the relative ratio of each guest residue X in the structural units (where applicable), and n describes the total length of the ELP in number of the structural repeats. For example, ELP1 [$V_5A_2G_3$-10] designates an ELP component containing 10 repeating units of the pentapeptide VPGXG (SEQ ID NO:3), where X is valine, alanine, and glycine at a relative ratio of 5:2:3; ELP1 [$K_1V_2F_1$-4] designates an ELP component containing 4 repeating units of the pentapeptide VPGXG (SEQ ID NO:3), where X is lysine, valine, and phenylalanine at a relative ratio of 1:2:1; ELP1 [$K_1V_7F_1$-9] designates a polypeptide containing 9 repeating units of the pentapeptide VPGXG (SEQ ID NO:3), where X is lysine, valine, and phenylalanine at a relative ratio of 1:7:1; ELP1 [$V_1A_8G_7$-10] designates an ELP component containing 10 repeating units of the pentapeptide VPGXG (SEQ ID NO:3), where X is valine, alanine, and glycine at a relative ratio of 1:8:7; ELP1 [V-5] designates a polypeptide containing 5 repeating units of the pentapeptide VPGXG (SEQ ID NO:3), where X is exclusively valine; ELP1 [V-20] designates a polypeptide containing 20 repeating units of the pentapeptide VPGXG (SEQ ID NO:3), where X is exclusively valine; ELP2 [5] designates a polypeptide containing 5 repeating units of the pentapeptide AVGVP (SEQ ID NO:4); ELP3 [V-5] designates a polypeptide containing 5 repeating units of the pentapeptide IPGXG (SEQ ID NO:5), where X is exclusively valine; ELP4 [V-5] designates a polypeptide containing 5 repeating units of the pentapeptide LPGXG (SEQ ID NO:7), where X is exclusively valine. Such ELP components as described in this paragraph may be used in connection with the present invention to increase the therapeutic properties of the therapeutic component.

Further, the Tt is a function of the hydrophobicity of the guest residue. Thus, by varying the identity of the guest residue(s) and their mole fraction(s), ELPs can be synthesized that exhibit an inverse transition over a 0-100° C. range. Thus, the Tt at a given ELP length may be decreased by incorporating a larger fraction of hydrophobic guest residues in the ELP sequence. Examples of suitable hydrophobic guest residues include valine, leucine, isoleucine, phenylalanine, tryptophan and methionine. Tyrosine, which is moderately hydrophobic, may also be used. Conversely, the Tt may be increased by incorporating residues, such as those selected from the group consisting of: glutamic acid, cysteine, lysine, aspartate, alanine, asparagine, serine, threonine, glycine, arginine, and glutamine; preferably selected from alanine, serine, threonine and glutamic acid.

The ELP component in some embodiments is selected or designed to provide a Tt (under physiological conditions) ranging from about 10 to about 80° C., such as from about 35 to about 60° C., or from about 38 to about 45° C. In some embodiments, the Tt is greater than about 40° C. or greater than about 42° C., or greater than about 45° C., or greater than about 50° C. The transition temperature, in some embodiments, is above the body temperature of the subject or patient (e.g., >37° C.) thereby remaining soluble in vivo, or in other embodiments, the Tt is below the body temperature (e.g., <37° C.) to provide alternative advantages, such as in vivo formation of a drug depot for sustained release of the therapeutic agent. See, for example, US 2007/0009602, which is hereby incorporated by reference in its entirety.

The Tt of the ELP component can be modified by varying ELP chain length, as the Tt generally increases with decreasing MW. For polypeptides having a molecular weight >100,000, the hydrophobicity scale developed by Urry et al. (PCT/US96/05186, which is hereby incorporated by reference in its entirety) provides one means for predicting the approximate Tt of a specific ELP sequence. However, in some embodiments, ELP component length can be kept relatively small, while maintaining a target Tt, by incorporating a larger fraction of hydrophobic guest residues (e.g., amino acid residues having hydrophobic side chains) in the ELP sequence. For polypeptides having a molecular weight <100,000, the Tt may be predicted or determined by the following quadratic function: $Tt=M_0+M_1X+M_2X^2$ where X is the MW of the fusion protein, and $M_0=116.21$; $M_1=-1.7499$; $M_2=0.010349$.

While the Tt of the ELP component, and therefore of the ELP component coupled to a therapeutic component, is affected by the identity and hydrophobicity of the guest residue, X, additional properties of the molecule may also be affected. Such properties include, but are not limited to solubility, bioavailability, persistence, half-life, potency and safety of the molecule.

In the Examples section below, it is seen that the ELP-coupled VIP agent retains a significant amount of the native VIP's biological activity, relative to unfused forms of VIP. Additionally, it is shown that ELPs exhibit long half-lives. Correspondingly, ELPs can be used in accordance with the invention to substantially increase (e.g. by greater than 10%, 20%, 30%, 50%, 100%, 200% or more, in specific embodiments) the half-life of VIP, as conjugated with an ELP, in comparison to the half-life of the free (unconjugated) form of the therapeutic agent. The modified VIP having extended circulatory half-life may be administered from 1 to about 10 times per week, such as from 1 to about 5, or 1 to about 3 times per week. The modified VIP or pharmaceutical composition comprising the same may be administered about once daily, or about every other day, or about every third day, or about once a week (i.e. once weekly dosing).

Conjugation and Coupling

A recombinantly-produced VIP fusion protein, in accordance with certain embodiments of the invention, includes the fusion component (e.g., ELP) and a VIP or an analog of VIP associated with one another by genetic fusion. For example, the fusion protein may be generated by translation of a polynucleotide encoding VIP or an analog of VIP cloned in-frame with the ELP component.

In certain embodiments, the ELP component and VIP or an analog of VIP can be fused using a linker peptide of various lengths to provide greater physical separation and allow more spatial mobility between the fused portions, and thus maximize the accessibility of VIP or an analog of VIP, for instance, for binding to its cognate receptor. The linker peptide may consist of amino acids that are flexible or more rigid. For example, a flexible linker may include amino acids having relatively small side chains, and which may be hydrophilic. Without limitation, the flexible linker may comprise glycine and/or serine residues. More rigid linkers may contain, for example, more sterically hindering amino acid side chains, such as (without limitation) tyrosine or histidine. The linker may be less than about 50, 40, 30, 20, 10, or 5 amino acid residues. The linker can be covalently linked to and between VIP or an analog of VIP and an ELP component, for example, via recombinant fusion.

The linker or peptide spacer may be protease-cleavable or non-cleavable. By way of example, cleavable peptide spacers include, without limitation, a peptide sequence recognized by proteases (in vitro or in vivo) of varying type, such as Tev, thrombin, factor Xa, plasmin (blood proteases), metalloproteases, cathepsins (e.g., GFLG, SEQ ID NO: 47, etc.), and proteases found in other corporeal compartments. In some embodiments employing cleavable linkers, the fusion protein may be inactive, less active, or less potent as a fusion, which is then activated upon cleavage of the spacer in vivo. Alternatively, where the therapeutic agent is sufficiently active as a fusion, a non-cleavable spacer may be employed. The non-cleavable spacer may be of any suitable type, including, for example, non-cleavable spacer moieties having the formula [(Gly)n-Ser]m, where n is from 1 to 4, inclusive, and m is from 1 to 4, inclusive. Alternatively, a short ELP sequence different than the backbone ELP could be employed instead of a linker or spacer, while accomplishing the necessary effect.

In still other embodiments, the therapeutic agent is a recombinant fusion having a therapeutic component flanked on each terminus by an ELP component. At least one of said ELP components may be attached via a cleavable spacer, such that the therapeutic component is inactive, but activated in vivo by proteolytic removal of a single ELP component. The resulting single ELP fusion being active, and having an enhanced half-life (or other property described herein) in vivo.

In other embodiments, the present invention provides chemical conjugates of a VIP or an analog of VIP and the ELP component. The conjugates can be made by chemically coupling an ELP component to VIP or an analog of VIP by any number of methods well known in the art (See e.g. Nilsson et al., 2005, *Ann Rev Biophys Bio Structure* 34: 91-118). In some embodiments, the chemical conjugate can be formed by covalently linking VIP or an analog of VIP to the ELP component, directly or through a short or long linker moiety, through one or more functional groups on the therapeutic proteinacious component, e.g., amine, carboxyl, phenyl, thiol or hydroxyl groups, to form a covalent conjugate. Various conventional linkers can be used, e.g., diisocyanates, diisothiocyanates, carbodiimides, bis (hydroxysuccinimide) esters, maleimide-hydroxysuccinimide esters, glutaraldehyde and the like.

Non-peptide chemical spacers can additionally be of any suitable type, including for example, by functional linkers described in Bioconjugate Techniques, Greg T. Hermanson, published by Academic Press, Inc., 1995, and those specified in the Cross-Linking Reagents Technical Handbook, available from Pierce Biotechnology, Inc. (Rockford, Ill.), the disclosures of which are hereby incorporated by reference, in their respective entireties. Illustrative chemical spacers include homobifunctional linkers that can attach to amine groups of Lys, as well as heterobifunctional linkers that can attach to Cys at one terminus, and to Lys at the other terminus.

In certain embodiments, relatively small ELP components (e.g., ELP components of less than about 30 kDa, 25 kDa, 20 kDa, 15 kDa, or 10 kDa), that do not transition at room temperature (or human body temperature, e.g., Tt>37° C.), are chemically coupled or crosslinked. For example, two relatively small ELP components, having the same or different properties, may be chemically coupled. Such coupling, in some embodiments, may take place in vivo, by the addition of a single cysteine residue at or around the C-terminus of the ELP. Such ELP components may each be fused to one or more therapeutic components, so as to increase activity or avidity at the target.

Polynucleotides, Vectors, Host Cells, and Methods for Production

In another aspect, the invention provides polynucleotides comprising a nucleotide sequence encoding the modified VIP of the invention. Such polynucleotides may further comprise, in addition to sequences encoding VIP or VIP analog and fusion sequences, one or more expression control elements. For example, the polynucleotide may comprise one or more promoters or transcriptional enhancers, ribosomal binding sites, transcription termination signals, and polyadenylation signals, as expression control elements. The polynucleotide may be inserted within any suitable vector, which may be contained within any suitable host cell for expression, such as *E. coli*.

Generally, a vector comprising the polynucleotide can be introduced into a cell for expression of the therapeutic agent. The vector can remain episomal or become chromosomally integrated, as long as the insert encoding the therapeutic agent can be transcribed. Vectors can be constructed by standard recombinant DNA technology. Vectors can be plasmids, phages, cosmids, phagemids, viruses, or any other types known in the art, which are used for replication and expression in prokaryotic or eukaryotic cells. It will be appreciated by one of skill in the art that a wide variety of components known in the art (such as expression control elements) may be included in such vectors, including a wide variety of transcription signals, such as promoters and other sequences that regulate the binding of RNA polymerase onto the promoter. Any promoter known to be effective in the cells in which the vector will be expressed can be used to initiate expression of the therapeutic agent. Suitable promoters may be inducible or constitutive.

In certain embodiments, the modified VIP is expressed from *E. coli* or other bacterial expression system. *E. coli* generally will not remove N-terminal methionine during expression, such that the modified VIP molecule maintains receptor specificity. Other expression systems may be employed in accordance with the invention, including yeast expression systems, mammalian cell expression systems, and baculovirus systems.

The therapeutic protein, when employing ELP fusion sequences, may be recovered by inverse temperature cycling. Specifically, as previously described, the ELP component undergoes a reversible inverse phase transition. That is, the ELP components are structurally disordered and highly soluble in water below a transition temperature (Tt), but exhibit a sharp (2-3° C. range) disorder-to-order phase transition when the temperature is raised above the Tt, leading to desolvation and aggregation of the ELP components. For example, the ELP forms insoluble polymers, when reaching sufficient size, which can be readily removed and isolated from solution by centrifugation. Such phase transition is reversible, and isolated insoluble ELPs can be completely resolubilized in buffer solution when the temperature is returned below the Tt of the ELPs. Thus, the therapeutic agents of the invention can, in some embodiments, be separated from other contaminating proteins to high purity using inverse transition cycling procedures, e.g., utilizing the temperature-dependent solubility of the therapeutic agent, or salt addition to the medium. Successive inverse phase transition cycles can be used to obtain a high degree of purity. In addition to temperature and ionic strength, other environmental variables useful for modulating the inverse transition of the therapeutic agents include pH, the addition of inorganic and organic solutes and solvents, side-chain ionization or chemical modification, and pressure.

Pharmaceutical Compositions and Methods of Administration

The present invention further provides pharmaceutical compositions comprising an effective amount of the modified VIP of the invention (as described above) together with a pharmaceutically acceptable carrier, diluent, or excipient. Such pharmaceutical compositions are effective for treating or ameliorating, for example, autoimmune or inflammatory disease, as described herein.

The therapeutic agents of the invention may be administered per se as well as in various forms including pharmaceutically acceptable esters, salts, and other physiologically functional derivatives thereof. In such pharmaceutical formulations, the therapeutic agents can be used solely, or together (including formulated with) other therapeutic ingredients, such as anti-inflammatory agents or immunosuppressants.

The carrier(s) must be pharmaceutically acceptable in the sense of being compatible with the other ingredients of the formulation and not unduly deleterious to the recipient thereof.

The formulations of the therapeutic agent include those suitable for parenteral as well as non-parenteral administration. Exemplary administration modalities include oral, buccal, topical, nasal, subcutaneous, intramuscular, and intravenous, among others. Formulations suitable for parenteral administration are preferred.

The formulations comprising the therapeutic agent of the present invention may conveniently be presented in unit dosage forms and may be prepared by any of the methods well known in the art of pharmacy. Such methods generally include the step of bringing the therapeutic agents into association with a carrier which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation.

Formulations suitable for parenteral administration conveniently comprise a sterile aqueous preparation of the therapeutic agent, which preferably is isotonic with the blood of the recipient (e.g., physiological saline solution). Such formulations may include suspending agents and thickening agents or other microparticulate systems which are designed to target the therapeutic agent to the circulation or one or more organs. The formulations may be presented in unit-dose or multi-dose form.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like.

While one of skill in the art can determine the desirable dose in each case (including a unit dose for depot administration), a suitable dose of the therapeutic agent for achievement of therapeutic benefit, may, for example, be in a range of about 1 microgram (µg) to about 100 milligrams (mg) per kilogram body weight of the recipient, or in a range of about 10 µg to about 50 mg per kilogram body weight, or in a range of about 10 µg to about 10 mg per kilogram body weight. The desired dose may be presented as one dose or two or more sub-doses administered at appropriate intervals throughout the dosing period (e.g., one week, two weeks, etc. . . . ). These sub-doses can be administered in unit dosage forms, for example, containing from about 10 µg to about 500 mg, or from about 50 µg to about 200 mg, or from about 50 µg to about 100 mg of active ingredient per unit dosage form. Alternatively, if the condition of the recipient so requires, the doses may be administered as a continuous infusion.

The mode of administration and dosage forms will of course affect the therapeutic amount of the peptide active therapeutic agent that is desirable and efficacious for a given treatment application. For example, orally administered dosages can be at least twice, e.g., 2-10 times, the dosage levels used in parenteral administration methods. Depot formulations will also allow for significantly more therapeutic agent to be delivered, such that the agent will have a sustained release over time.

VIP that circulates in the plasma of normal individuals originates from VIP-containing nerve fibers in the gastrointestinal tract and also reflects peptide overflow from vascular nerves (Cugini et al., 1991, *Reg Pept* 34: 141-8). Like most vasoactive proteins, VIP has a relatively short half-life. The half-life of VIP in blood is less than 2 minutes (Domschke et al., 1978, Gut 19: 1049-53; Burhol et al., 1978, *Scand J Gastroent* 13: 807-813). One advantage of the modified VIPs described herein is extended half-life or persistence in the body. In accordance with certain embodiments of the invention, the VIP may be administered from 1 to about 10 times per week, such as from 1 to about 5, or 1 to about 3 times per week. The modified VIP or pharmaceutical composition comprising the same may be administered about once daily, or about every other day, or about every third day, or about once a week.

In certain embodiments, the modified VIP is administered parenterally, such as by subcutaneous or intramuscular injection. The administration may be a unit dose of the modified VIP as described herein.

The modified VIP, when administered parenterally, may be administered once per day, or once or twice per week, or from once to five times per month. In these embodiments, the modified VIP may be administered as a soluble fusion peptide, that persists in the circulation, as described herein, to provide sustained activity with relatively infrequent administration. The modified VIP may be administered as a drug depot, as also described herein, to provide a sustained release of fusion peptide into the circulation over time. See US 2007/0009602, which is hereby incorporated by reference.

Methods of Use

In other aspects, the invention provides methods of treating, ameliorating, or preventing a condition in a mammal. Such conditions include a variety of cardiovascular, immunological (e.g., autoimmune), and neurological conditions. For example, the modified VIP may be used to adjust the balance between pro-inflammatory and anti-inflammatory effectors in a patient, including a patient suffering from an autoimmune disease or inflammatory condition. Exemplary indications for the modified VIP include hypertension, myocardial fibrosis, heart failure, cardiomyopathy, diabetes, chronic obstructive pulmonary disease (COPD), arthritis, inflammatory bowel disease (IBD), Parkinson's disease, brain trauma, and asthma, among others.

The invention thus provides a method for treating a variety of conditions, including conditions characterized by autoimmunity or inflammation. The method comprises administering an effective amount of the modified VIP of the invention to a patient in need.

Hypertension

In various embodiments described herein, the present invention provides methods of treating or preventing hypertension in a patient in need, comprising administering an effective amount of the modified VIP. Forms of hypertension treatable with the modified VIPs of the present invention include pulmonary hypertension, uncontrolled essential hypertension, and resistant hypertension.

Pulmonary hypertension is a relatively rare but highly fatal disease characterized by progressive pulmonary arterial hypertension and increased thickening of smaller pulmonary arteries and arterioles, culminating in right ventricular (RV) failure (Said et al., 2007, *Circulation* 115: 1260-8). VIP has been linked to pulmonary and systemic circulation. With respect to the pulmonary vascular bed and its alterations in pulmonary hypertension, VIP relaxes pulmonary vascular smooth muscle from several mammalian species in vitro, neutralizes or attenuates the actions of endothelin and other vasoconstrictors, reduces hypoxic pulmonary vasoconstriction, and inhibits the proliferation of pulmonary vascular smooth muscle from patients with pulmonary hypertension. Furthermore, VIP is a cotransmitter of the physiological nonadrenergic, noncholinergic system of pulmonary vascular smooth muscle relaxation. Moreover, VIP-containing nerves, normally plentiful in the pulmonary artery, have been reported to be absent in pulmonary arteries from patients with pulmonary hypertension, and inhalation of the peptide had a beneficial therapeutic effect on those patients (Petkov et al., 2003, *J. Clin Invest.* 111: 1339-1346). Finally, studies have shown that VIP replacement therapy in VIP$^{-/-}$ mice is capable of preventing or at least slowing the progression of key pathological changes in pulmonary hypertension (Said et al., 2007, *Circulation* 115: 1260-8). Thus, application of VIP to patients with pulmonary hypertension can be expected to result in substantial improvement of hemodynamic and prognostic parameters of the disease (Petkov et al., 2003, *J. Clin Invest.* 111: 1339-1346).

Uncontrolled essential hypertension is blood pressure that is consistently higher than normal when no cause for the high blood pressure can be found. Essential hypertension is the most prevalent hypertension type, affecting 90-95% of hypertensive patients (Carretero et al., 2000, *Circulation* 101: 329-35) and experts believe it is caused by several undiscovered factors. Concentrations of VIP are decreased in stroke-prone, essential hypertensive rats (Mori et al., 1993, *Jpn Heart J.* 34: 785-94) and use of human VIP with sterically stabilized liposomes can normalize systemic arterial pressure in spontaneously hypertensive hamsters (Onyuksel et al., 2006, *Peptides* 27: 2271-5).

Resistant hypertension is a form of high blood pressure that does not respond to treatment (i.e. blood pressure remains high even when a combination of drugs is administered). The causes of poor blood pressure control are numerous. The most likely causes are volume overload either due to excess sodium intake, intolerance to medications, noncompliance and secondary hypertension (Graves J W, 2000, *Mayo Clin Prac* 75: 278-84). As a potent systemic vasodilator, VIP has utility for the treatment and prevention of hypertension in patients producing the hallmarks of resistant hypertension.

Heart Disease

In additional embodiments, the present invention provides methods of treating or preventing heart disease in a patient in need, comprising administering an effective amount of the modified VIP. Forms of heart disease treatable with the modified VIPs of the present invention include myocardial fibrosis, heart failure, and cardiomyopathy.

Changes in the synthesis and secretion of VIP in the heart appear to play a role in the pathogenesis of several diseases, such as heart failure and myocardial fibrosis (Dvoráková M C, 2005, *Drug News Perspect.* 18: 387-91). For instance, the concentration of VIP is decreased significantly in both tissue from patients with cardiomyopathy and in cardiac tissue from animal models of heart failure (Unverferth et al., 1986, *J. Lab Clin Med* 108: 11-16). Furthermore, degradation of VIP is increased in hearts with fibrosis and consequently myocardial VIP concentration decreases. Thus, decreased VIP appears to be an important factor in the pathogenesis of the disease (Ye et al., 2003, *Acta Physiol Scand* 179: 353-60) and decreased VIP concentrations are associated with a progressive worsening of heart failure. The use of the vasopeptidase inhibitor omapatrilat, which is known to decrease the metabolic clearance rate of VIP, resulted in a decrease in systolic blood pressure as well as in a decrease in myocardial fibrosis when compared to control (Ye et al., 2004, *Eur J Pharmacol* 485: 235-42). A protective effect of VIP was also reported in ischemic and repurfused myocardium (Kalfin et al., 1994, *J Pharmacol Exp Ther* 268: 952-8). Therefore, application of the modified VIPs of the present invention can be expected to have a beneficial effect in a variety of pathological conditions, including heart failure, cardiomyopathy, and myocardial fibrosis.

Type 2 Diabetes Mellitus

In additional embodiments, the present invention provides methods of treating or preventing diabetes in a patient in need, comprising administering an effective amount of the modified VIP. Specifically, the modified VIPs of the present invention have utility for the treatment and prevention of type 2 diabetes mellitus.

Studies have shown that the VIP content of the gastric astrum and duodenum of diabetic rats is significantly lower than that of normal rats (Gozes et al., 2004, *Best Pract Res Clin Endocrinol Metab* 18: 623-640). Low tissue levels of VIP in the gastroduodenal tract may contribute in part to the abnormal gut motility observed in diabetic patients (Adeghate et al., 2001, *Arch Phys Bioc* 109: 246-51). VIP stimulates insulin secretion from insulinoma cells, mouse pancreatic islets and perfused rat pancreas. Activation of VPAC1 has been implicated in elevating glucose output (Gozes et al., 2004, *Best Pract Res Clin Endocrinol Metab* 18: 623-640), whereas the VIP receptor VPAC2 is expressed in pancreatic islet β-cells and its activation causes an elevation of cyclic AMP and the stimulation of insulin secretion (DeSouza et al., 2009, *Nature Reviews* 8: 361-7). Furthermore, VIP stimulates glucagon secretion in humans, resulting in glucose release from the liver. Taken together, these studies reveal that VIP has extensive direct effects on glucose metabolism. Accordingly, VIP and modified forms of VIP, such as the fusion peptides disclosed herein, may be expected to be useful therapy for the treatment and prevention of type 2 diabetes.

VPAC2 Receptor Preference

In some embodiments, such as where the modified VIP has a higher preference for VPAC2 as compared to unmodified VIP, the modified VIP may reduce inflammatory responses, such as delayed-type hypersensitivity responses, in a patient. In some such embodiments, the modified VIP reduces the development of autoreactive T-cells. In these embodiments, the patient may have one or more conditions defined by TH1-type inflammation or TH1 autoimmunity, such as arthritis (including RA), Inflammatory Bowel Disease (e.g., Crohn's Disease), type 1 diabetes, multiple sclerosis, transplantation rejection, Sjogren's syndrome, pancreatitis, uveoretinitis, keratitis, and septic shock.

VPAC1 Receptor Preference

In some embodiments, such as where the modified VIP has a higher preference for VPAC1 as compared to unmodified VIP, the modified VIP may promote TH1 inflammatory responses, such as delayed-type hypersensitivity responses, in a patients. In these embodiments, the patient may have one or more conditions associated with TH2 immunity, such as asthma or chronic obstructive pulmonary disease (COPD).

COPD is a chronic inflammatory disease of the airways, which affects as many as 8% of individuals in industrialized nations. There is an increase in the number of woman and men suffering from COPD. Pulmonary hypertension is a common symptom of chronic airflow obstruction, but the precise mechanisms of increased vascular resistance are unclear. Potential causes of pulmonary hypertension in COPD include emphysematous destruction of the capillary bed, remodeling of pulmonary vessels and hypoxic pulmonary vasoconstriction.

VIP is one of the most abundant molecules found in the respiratory tract. Due to its anti-inflammatory and bronchodilatory properties, it has been proposed as a novel treatment for COPD and asthma. Although VPAC1 up-regulation is dominant, both VPAC1 and VPAC2 are necessary for optimal anti-inflammatory signaling (Burian et al., 2010, *Pep-* tides 31: 603-8). Accordingly, treatment with VIP and modified forms of VIP, such as the fusion peptides disclosed herein, may be expected to help decrease the chronic inflammation in the lung of COPD and asthma patients.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1

Cloning of VIP-ELP Constructs

The DNA sequence for the VIP peptide was as described in Simoncsits et al. (*Synthesis, cloning and expression in Escherichia coli of artificial genes coding for biologically active elongated precursors of the vasoactive intestinal polypeptide, Eur. J. Biochem.* 1988, 178(2):343-350, which is herein incorporated by reference in its entirety for all purposes), except that residue 17 was the native methionine and did not have either of the described C-terminal extensions (See SEQ ID NO. 16).

Two initial variants were made, one with a methionine at the N-terminus, due to the required ATG start codon, (PB1046, SEQ ID NO. 17) and one with the tripeptide MAA at the N-terminus (PB1047, SEQ ID 18). The methionine on PB1046 would normally be removed by methionine aminopeptidase (MA) but as histidine is the second residue and one of the least favored amino acids at this position for MA, the methionine is not removed. The methionine on PB1047 was removed to leave AA, which can then be removed in vitro or in vivo by DPPIV to give the histidine as the N-terminal residue. The VIP DNA sequence was cloned into vector pPB1031 (see FIG. 3) carrying the ELP1-120 DNA sequence to give an expression cassette under the control of the T7 promoter.

Figure 4:
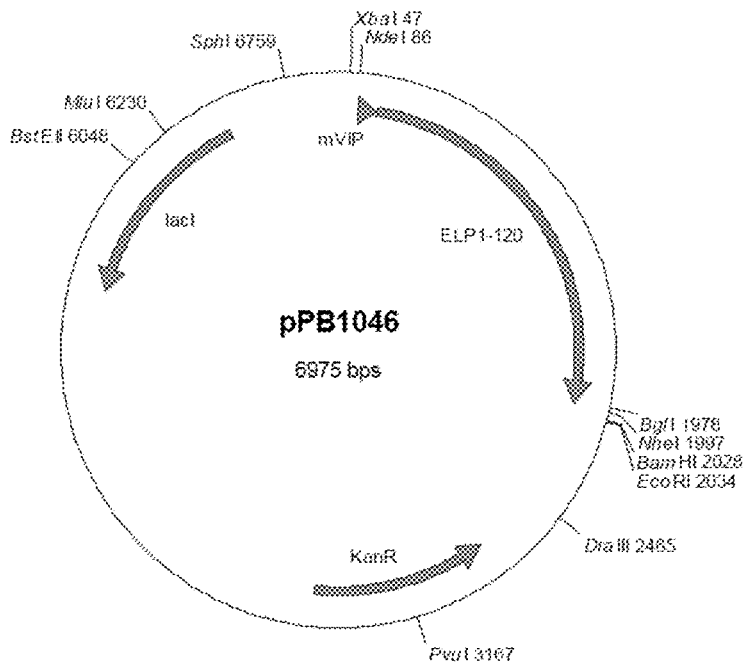
FIG. 4 depicts pPB1046 encoding an M-VIP-ELP1-120 (SEQ ID NOs: 39 and 40) fusion protein. Primers (P0045, SEQ ID NO: 31, P0048, SEQ ID NO: 32, and P0065, SEQ ID NO: 34) for construction of the recombinant gene are shown.

The synthetic oligonucleotides P0045 (SEQ ID NO. 31), P0048 (SEQ ID NO. 32), P0064 (SEQ ID NO. 33) and P0065 (SEQ ID NO. 34) were annealed together, digested with the restriction enzyme XbaI and ligated into the plasmid pPB1031 which had been digested with the restriction enzymes XbaI/KpnI to give expression plasmid pPB1046 (see FIG. 4).

Figure 5:
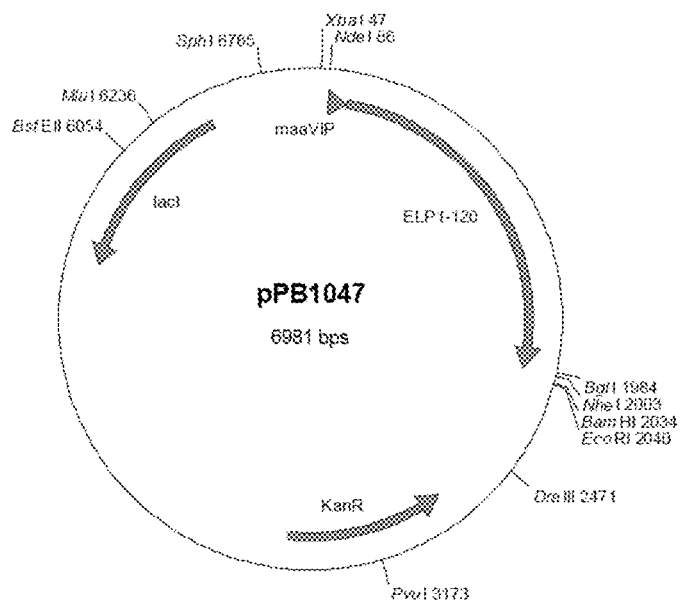
FIG. 5 depicts pPB1047 encoding an MAA-VIP-ELP1-120 (SEQ ID NOs: 41 and 42) fusion protein. Primers (P0066, SEQ ID NO: 35, P0064, SEQ ID NO: 33, P0067, SEQ ID NO: 36) for construction of the recombinant gene are shown.

The synthetic oligonucleotides P0066 (SEQ ID NO. 35), P0064 (SEQ ID NO. 33), P0067 (SEQ ID NO. 36) and P0065 (SEQ ID NO. 34) were annealed together, digested with the restriction enzyme XbaI and ligated into the plasmid pPB1031 which had been digested with the restriction enzymes XbaI/KpnI to give expression plasmid pPB1047 (see FIG. 5).

Figure 6:
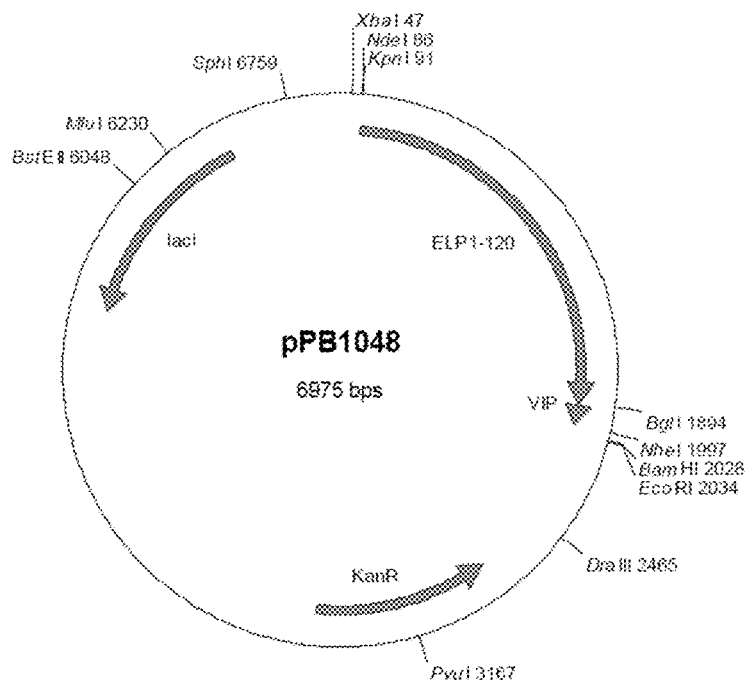
FIG. 6 depicts pPB1048 encoding an ELP1-120-VIP (SEQ ID NOs: 43 and 44) fusion protein. Primers for constructing the recombinant gene (P0068, SEQ ID NO: 37, P0069, SEQ ID NO: 38) are shown.

In addition, and assuming that the N-terminus was not an absolute requirement for activity, a C-terminal fusion was also made, pPB1048 (see FIG. 6). The synthetic oligonucleotides P0068 (SEQ ID NO. 37) and P0069 (SEQ ID NO. 38) were annealed together and ligated into the plasmid pPB1031 which had been digested with the restriction enzymes BglI/NheI to give the expression plasmid pPB1048.

Example 2

Expression of VIP-ELP Constructs

Figure 7:
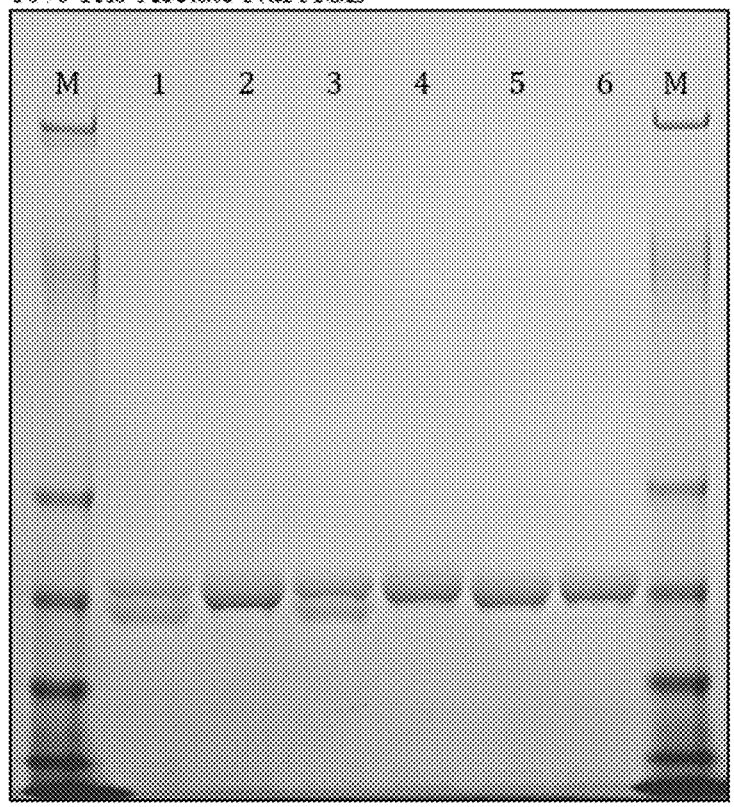
FIG. 7 is a 10% Tris-Acetate NuPAGE gel analysis of purified VIP-ELP fusion proteins, with or without heat denature.

The *E. coli* production strain BLR (Novogen) was transformed with the plasmids pB1046, pPB1047 and pPB1048 and grown in rich medium in shake flasks at 37° C. overnight. The cell pellets were resuspended in TE pH 8.0 buffer, lysed through a microfluidizer (Microfluidics), centrifuged to remove the insoluble material and the product purified from the resulting soluble lysate by 'transitioning' (ref) with the addition of NaCl to 3M. The samples were taken through a further two rounds of transitioning to give the final purified samples. These were analyzed by SDS-PAGE and PB1046 and PB1047 were found to give two bands (see FIG. 7). Assuming this was as a result of proteolysis the cultures were grown again but this time, before lysis, were heated to 60° C. of 15 minutes. Analysis by 10% Tris-Acetate NuPAGE gel indicted that the proteolysis had been inhibited (see FIG. 7).

The proteolysis was, most likely, within the peptide and probably close to the junction of peptide and ELP as no breakdown was seen on the C-terminal fusion PB1048. That proteolysis could be prevented by heat denaturing of protease(s) before lysis of the cells, which would tend to implicate a periplasmic protease(s) rather than a cytosolic protease, or a cytosolic protease that was activated or behaves differently upon lysis.

Example 3

Activity of Modified VIP-ELP Fusion Protein In Vitro

To measure the in vitro biological activity and potency of VIP or VIP-ELP fusion proteins, a cell-based bioassay was used. The assay measures the increase in intracellular cyclic adenosine monophosphate (cAMP) concentration in response to treatment with VIP or VIP-ELP fusion proteins in Chinese Hamster Ovary (CHO) cells that have been engineered to express either the human Vasoactive Intestinal Peptide Receptor 2 (VPAC2) or the human Vasoactive Intestinal Peptide Receptor 1 (VPAC1). Both VIP and VIP-ELP fusion proteins can stimulate production of cAMP in these cells, indicating that the fusion proteins retain the ability to bind and activate the receptor. Since the amount of cAMP accumulation in cells after receptor-mediated ligand binding and activation is directly proportional to the amount of intact peptide or fusion protein present, the assay can be used to determine bioactivity and relative potency.

Figure 8:
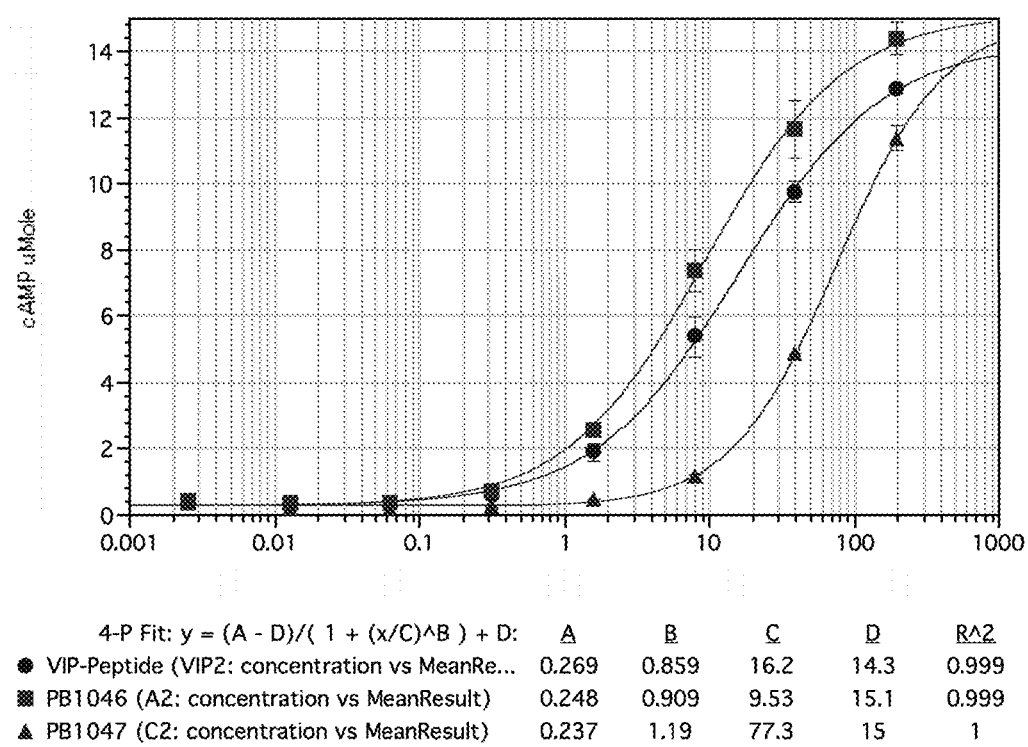
FIG. 8 shows the in vitro activity of native VIP and VIP-ELP fusion proteins PB1046 and PB1047 for VPAC2 receptor.

In this example, the activity of VIP-ELP fusion proteins PB1046 and PB1047 was tested. Construct PB1046 contains VIP with a Met at the N-terminus and construct PB1047 contains VIP with Ala-Ala at its N-terminus. Both constructs have ELP(1-120) at their C-terminus. In the first experiment, the activity of the constructs was tested using CHO cells expressing the VIP receptor VPAC2. After 30 minute incubations of various concentrations of the fusion proteins with the cell, the cells were lysed and the amount of cAMP produced was measured using a commercial kit. PB1047 was DPP-IV treated prior to the addition to the cells. FIG. 8 shows the result. As shown, modified VIP fusion protein PB1046 is somewhat more active than native VIP protein, while PB1047 is less active.

Figure 9:
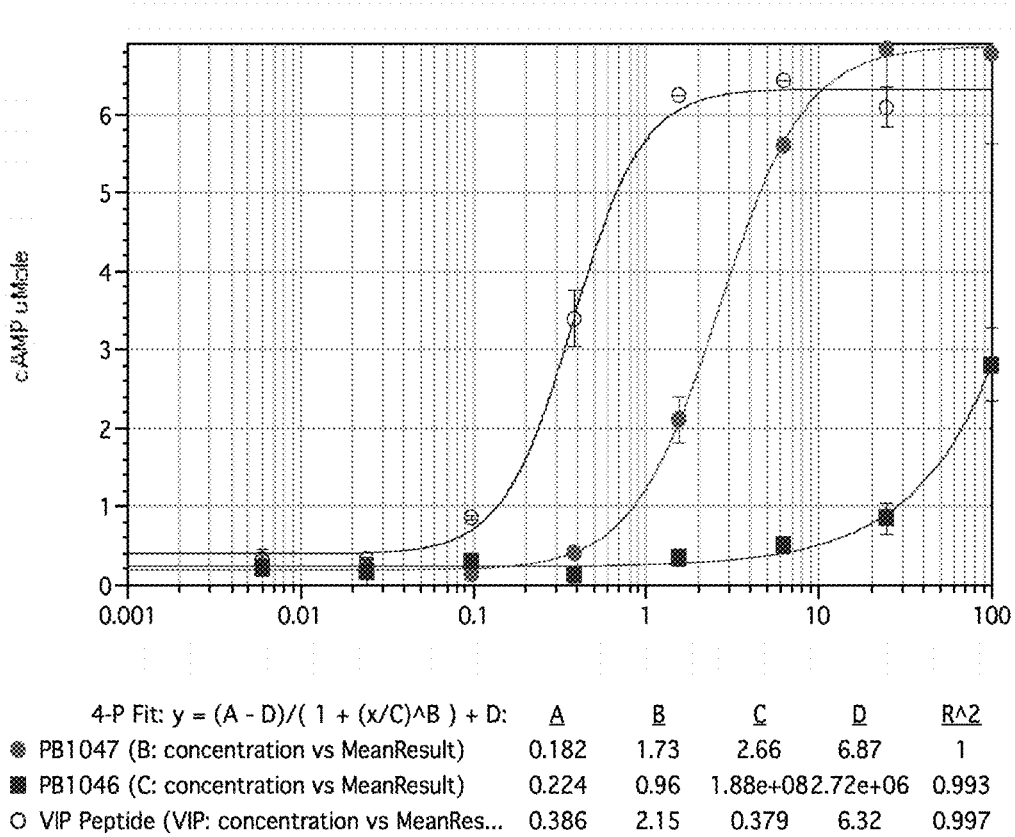
FIG. 9 shows the in vitro activity of native VIP and VIP-ELP fusion proteins PB1046 and PB1047 for VPAC1 receptor.

The activity of PB1046 and PB1047 was also tested using CHO cells expressing the VIP receptor VPAC1. After 30 minute incubations of various concentrations of the fusion proteins with CHO cells, cells were lysed and the amount of cAMP produced was measured using a commercial kit. PB1047 was DPP-IV treated prior to the addition to the cells. FIG. 9 shows the result. This time, modified VIP fusion protein PB1046 is much less active than native VIP protein, while the relative activity of PB1047 against native VIP is about the same as it was in the test for VPAC2 receptor. These results suggest that PB1046 selectively activates VPAC2 receptor over VPAC1 receptor.

Example 4

Blood Pressure Effect of VIP-ELP Fusion Protein

Figure 10:
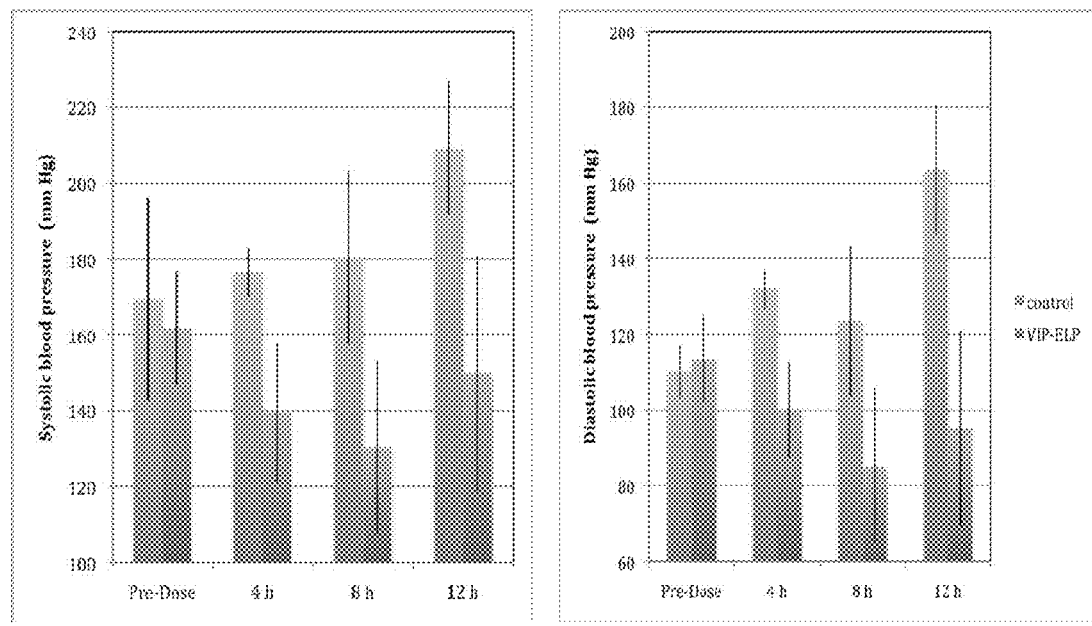
FIG. 10 shows the in vivo effect of the VIP-ELP fusion protein on rat blood pressure. Left panel shows systolic blood pressure. Right panel shows diastolic blood pressure. VIP-ELP lowers blood pressure for over a 12 hour period.

The activity of the modified VIP-ELP fusion protein PB1047 was also tested in vivo. Specifically, effects of VIP-ELP fusion protein on blood pressure were tested. Spontaneously hypertensive rats were treated subcutaneous with PB1047 (10 mg/kg) or buffer control and their blood pressures were measured at several points after administration of the fusion protein. Five animals were used for each group and the graphs show the average and the standard deviation. PB1047 significantly reduced systolic and diastolic blood pressure in these animals for at least 12 hours post administration (see FIG. 10), indicating that the VIP-ELP fusion protein is active, and can be potentially used as pharmaceuticals in treating VIP-related diseases.

Example 5

Additional VIP-ELP Fusion Proteins

DPP IV treatment of PB1047 resulted in removal of both AA and HS from the N-terminus, and inactivation of the peptide. Plasmid pPB1064 was therefore constructed, where the N-terminus was changed to MAAHG, SEQ ID NO: 45, instead of MAAHS, SEQ ID NO: 46, because HG is more resistant to DPP IV than HS.

Plasmid pPB1056 was also constructed, which encodes a VIP with an oppositely charged linker (SEQ ID NO. 20) based on the VPGXG, SEQ ID NO: 3, repeat before ELP.

Example 6

Cloning, Expression, and Analysis of an Additional VIP-ELP Fusion Protein, PB1120

Figure 11:
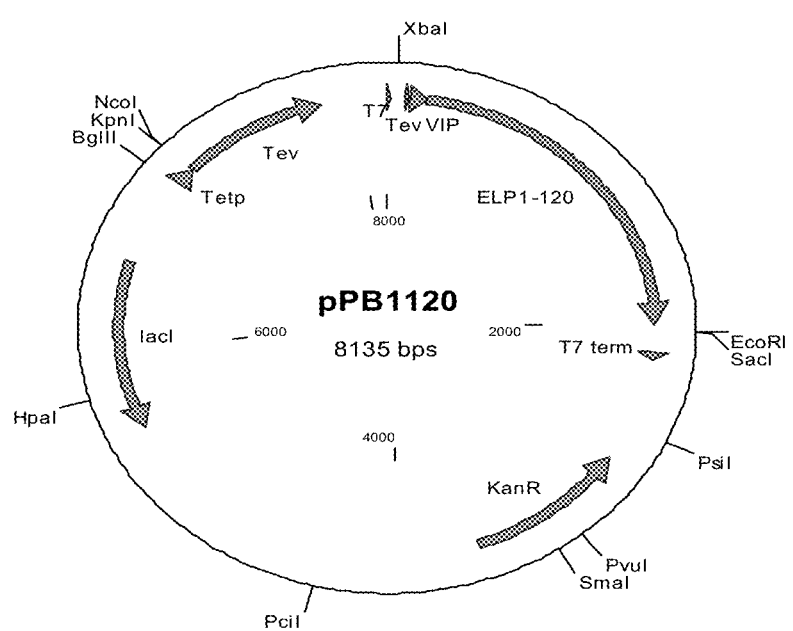
FIG. 11 is a plasmid map of pPB1120 (SEQ ID NO: 48), which encodes VIP-ELP1-120.

The VIP DNA sequence was cloned into vector pPB1120 (SEQ ID NO: 48) (see FIG. 11) carrying the ELP1-120 DNA sequence to give an expression cassette under the control of the T7 promoter. Next, the E. coli production strain BLR was transformed with the pPB1120 plasmid and grown in rich medium as described above. Samples of the resulting VIP-ELP1-120 fusion peptide, PB1120, were purified and analyzed via SDS-PAGE.

Figure 12:
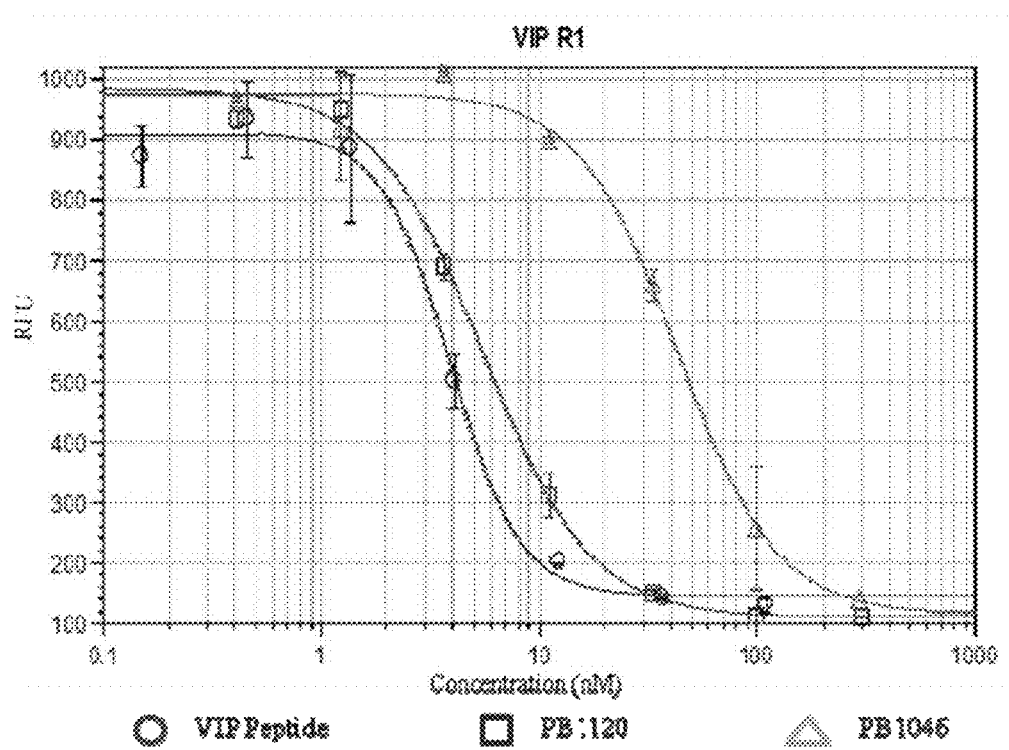
FIG. 12 shows the in vitro activity of native VIP and VIP-ELP fusion proteins PB1120 and PB1046 for VPAC1 receptor.

The activity of the PB1120 fusion peptide was tested in vitro. The activity was tested using an assay utilizing CHO cells expressing VIP receptor (VPAC1) as described above in Example 3. As FIG. 12 demonstrates, PB1120 was approximately 1.4 fold less active than the native VIP peptide on the VPAC1 receptor. By comparison, the construct PB1046 which contains an N-terminal methionine residue was approximately 11-fold less active than the native VIP peptide. Over the course of multiple experiments, PB1120 was anywhere from 1.4- to 6-fold less active than the native VIP peptide on the VPAC1 receptor.

Figure 13:
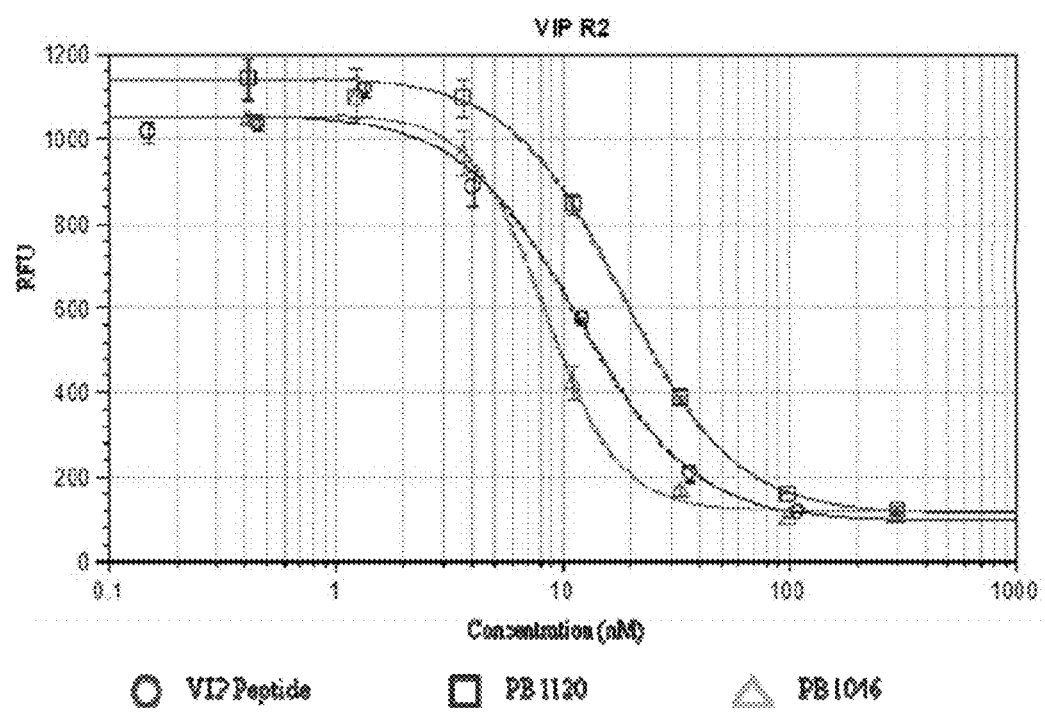
FIG. 13 shows the in vitro activity of native VIP and VIP-ELP fusion proteins PB1120 and PB1046 for VPAC2 receptor.

FIG. 13 illustrates the activity of PB1120 for the VPAC2 receptor. Like the results seen for the VPAC1 receptor, PB1120 show slightly less activity (~1.5 fold less) than the native VIP peptide for VPAC2. However, in contrast to the results seen with VPAC1, PB1046 was equipotent for VPAC2 as compared to the native peptide. Over the course of multiple experiments, PB1120 was anywhere from 1.5- to 7-fold less active than the native VIP peptide on the VPAC2 receptor.

Example 7

Pharmacokinetic Profile of Modified VIP-ELP Fusion Protein PB1120

Figure 14A:
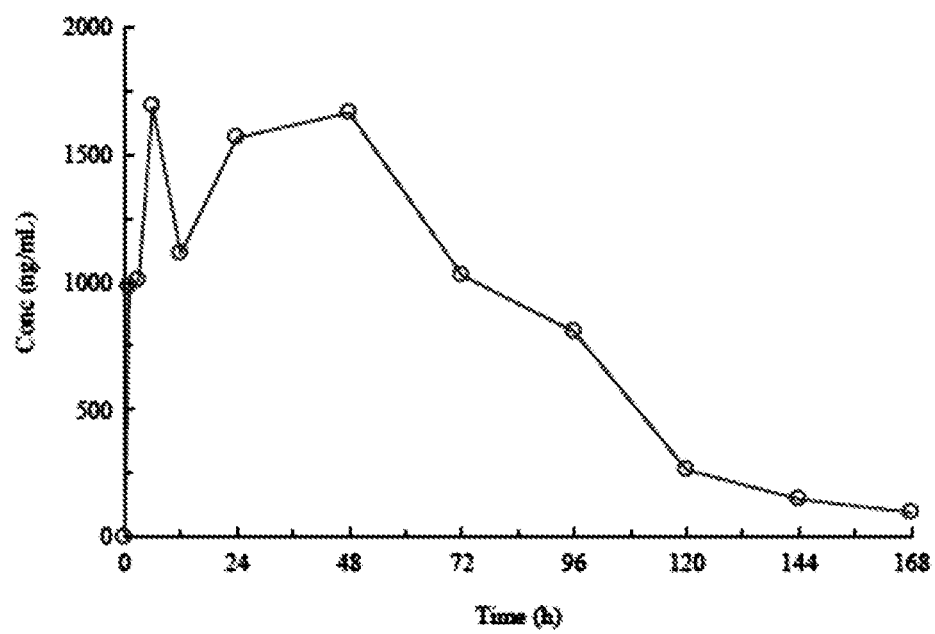
FIG. 14A shows the pharmacokinetic profile of the VIP-ELP fusion protein PB1120 in monkeys (n=3) following single subcutaneous injection of 3 mg/kg with linear axes.
Figure 14B:
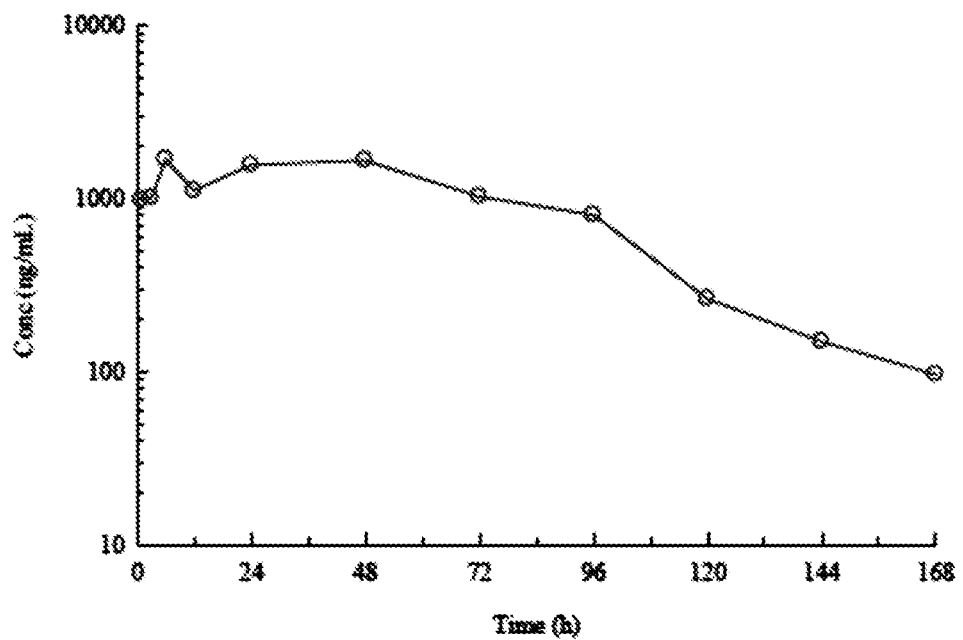
FIG. 14B shows the pharmacokinetic profile of the VIP-ELP fusion protein PB1120 with semi-logarithmic axes.

In addition to the biological potency assays described above, the pharmacokinetic profile of the VIP-ELP fusion protein PB1120 was also examined. Monkeys were given single subcutaneous (SC) injections (dosed at 3 mg/kg) of PB1120 and plasma drug concentrations were measured daily over the course of one week. Three animals were used and the graphs show the average and the standard deviation. More than half of the initial dose of PB1120 remained in the circulation to day 4 (see FIGS. 14A and 14B, which illustrate the mean plasma concentrations of PB1120 after SC administration using linear and semi-logarithmic axes, respectively).

Based upon this data, there appears to be a prolonged absorption phase after subcutaneous administration of PB1120, consistent with slow absorption from the site of administration. The apparent elimination half-life ($t\frac{1}{2}$), based on the decay of plasma concentrations, ranged from 9.9 to 45.8 h and likely reflects the slow absorption rather than true elimination. These data indicate that the VIP-ELP fusion protein has a dramatically extended half-life in comparison to native VIP and can potentially be administered at extended intervals (e.g. may be administered about once daily, about every other day, about every third day, or about once weekly).

Example 8

Effects of Modified VIP-ELP Fusion Protein PB1120 on Blood Pressure

Figure 15A:
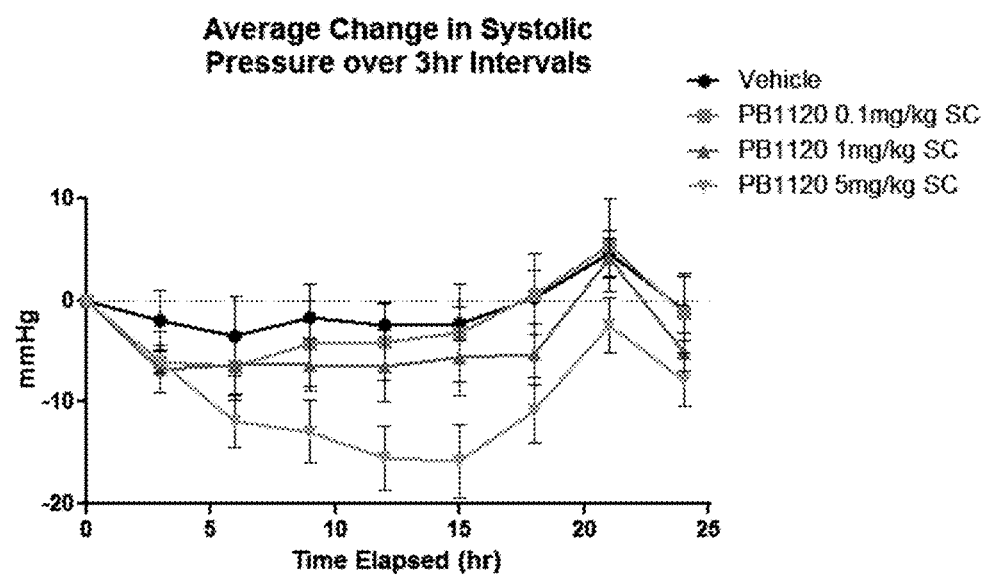
FIGS. 15A, 15B, and 15C show the average change in systolic, diastolic, and mean arterial pressure, respectively over 3 hr intervals in rats injected subcutaneously with PB1120 at 0.1 mg/kg, 1 mg/kg, or 5 mg/kg dosages.
Figure 15B:
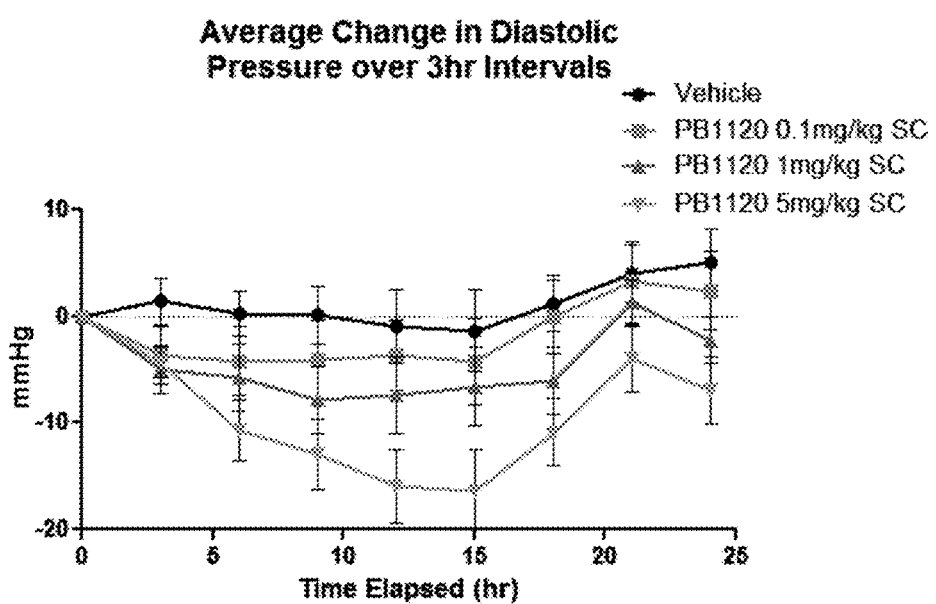
Figure 15C:
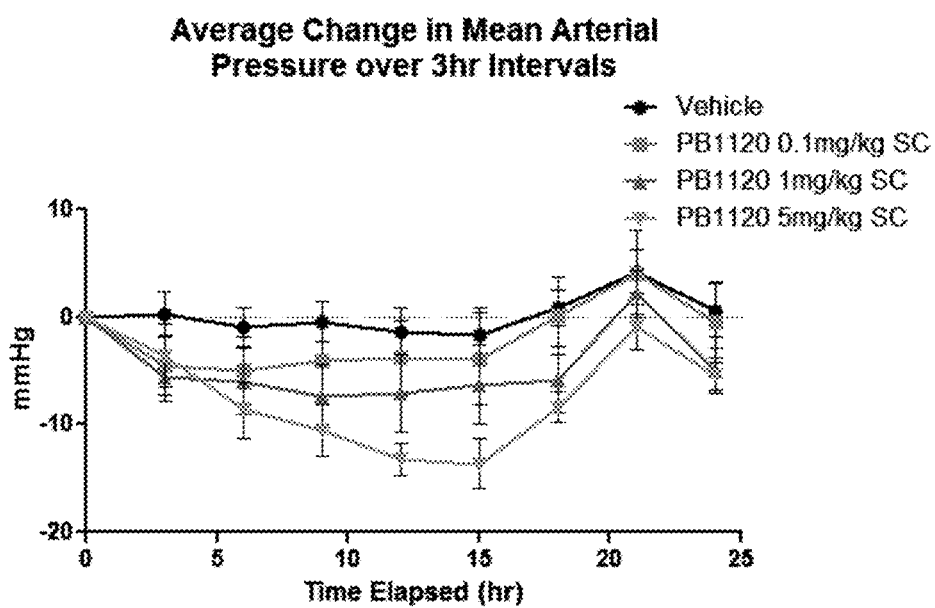
Figure 15D:
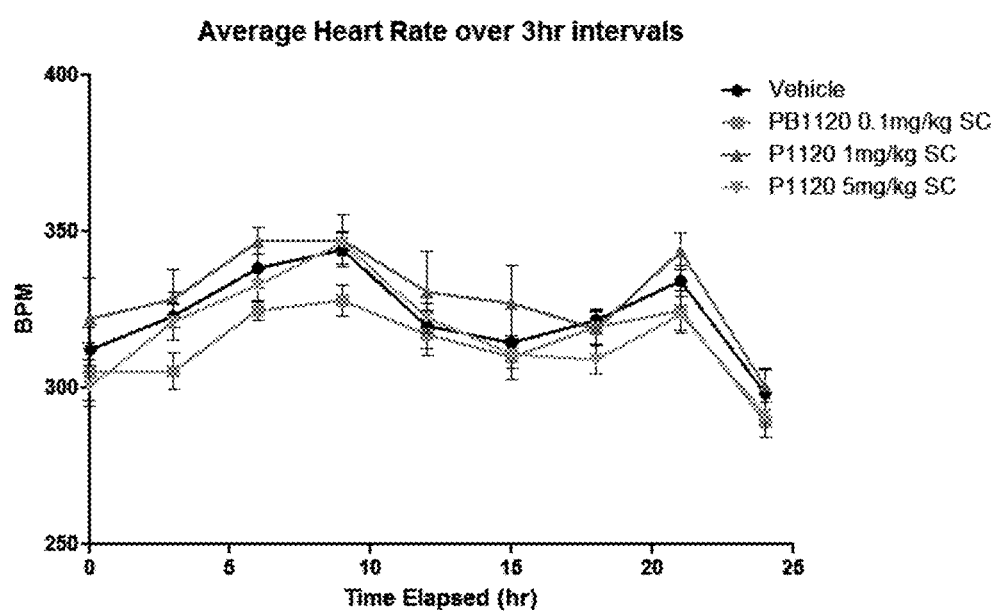
FIG. 15D shows the average heart rate of the subject rats over 3 hr intervals following administration of PB1120.

To measure the effects of the modified VIP-ELP fusion protein PB1120 on systolic, diastolic, and mean arterial blood pressure, rats were given single, subcutaneous injections of 0.1 mg/kg, 1 mg/kg, or 5 mg/kg of PB1120 and evaluated over 3-hr intervals. FIGS. 15A, 15B, and 15C show the average change in systolic, diastolic, and mean arterial pressure, respectively. FIG. 15D shows the average heart rate over 3 hr intervals following administration of PB1120. As FIGS. 15A-C demonstrate, rats injected with either 1 mg/kg or 5 mg/kg of PB1120 showed significant reductions in systolic, diastolic, and mean arterial pressure 9 hrs post-injection, indicating that VIP-ELP fusion protein PB1120 can potentially be administered for the purpose of treating or preventing hypertension in afflicted individuals.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A pharmaceutical composition for the treatment of heart disease, comprising a recombinant VPAC2-selective receptor agonist comprising the amino acid sequence of SEQ ID NO:13 having an N-terminal methionine increasing the preference of the agonist for VPAC2 versus VPAC1, and having an elastin-like polypeptide (ELP) at the C-terminus prolonging the absorption phase from an injection site and extending the circulatory half-life, and one or more pharmaceutically acceptable excipients, wherein the ELP comprises at least 60 repeat units of VPGXG (SEQ ID NO: 3), where X is independently selected from Val, Ala, and Gly.

2. The pharmaceutical composition of claim 1, wherein X is Val, Ala, and Gly in a ratio of 5:2:3.

3. The pharmaceutical composition of claim 1, wherein the pharmaceutical composition is administered parenterally.

4. The pharmaceutical composition of claim 3, wherein the pharmaceutical composition is administered subcutaneously, intramuscularly, or intravenously.

5. The pharmaceutical composition of claim 1, wherein the ELP comprises at least 120 repeat units of VPGXG (SEQ ID NO: 3), where X is independently selected from Val, Ala, and Gly.

6. The pharmaceutical composition of claim 5, wherein X is Val, Ala, and Gly in a ratio of 5:2:3.

7. The pharmaceutical composition of claim 1, wherein the VPAC2-selective receptor agonist comprises the amino acid sequence of SEQ ID NO:14.

8. The pharmaceutical composition of claim 1, wherein the heart disease is selected from the group consisting of myocardial fibrosis, heart failure, and cardiomyopathy.

9. A pharmaceutical composition for the treatment of heart disease, comprising a recombinant VPAC2-selective receptor agonist comprising the amino acid sequence of SEQ ID NO:13 having an N-terminal methionine increasing the preference of the agonist for VPAC2 versus VPAC1, and having an elastin-like polypeptide (ELP) at the C-terminus prolonging the absorption phase from an injection site and extending the circulatory half-life, and one or more pharmaceutically acceptable excipients, wherein the ELP comprises at least 60 units of VPGXG (SEQ ID NO:3), where X is Val, Ala, and Gly at a ratio of 5:2:3.

10. The pharmaceutical composition of claim 9, wherein the elastin-like-polypeptide comprises from 75 to 130 units of VPGXG (SEQ ID NO: 3).

11. The pharmaceutical composition of claim 10, wherein the elastin-like-polypeptide comprises 120 units of VPGXG (SEQ ID NO: 3).

12. The pharmaceutical composition of claim 9, wherein the pharmaceutical composition is administered parenterally.

13. The pharmaceutical composition of claim 12, wherein the pharmaceutical composition is administered subcutaneously, intramuscularly, or intravenously.

14. The pharmaceutical composition of claim 9, wherein the VPAC2-selective receptor agonist comprises the amino acid sequence of SEQ ID NO:14.

15. The pharmaceutical composition of claim 9, wherein the heart disease is selected from the group consisting of myocardial fibrosis, heart failure, and cardiomyopathy.

* * * * *

```
                        SEQUENCE LISTING

<160> NUMBER OF SEQ ID NOS: 50

<210> SEQ ID NO 1
<211> LENGTH: 4
<212> TYPE: PRT
<213> ORGANISM: Artificial Sequence
<220> FEATURE:
<223> OTHER INFORMATION: ELP tetrapeptide

<400> SEQUENCE: 1

Val Pro Gly Gly
1

<210> SEQ ID NO 2
<211> LENGTH: 4
<212> TYPE: PRT
<213> ORGANISM: Artificial Sequence
<220> FEATURE:
<223> OTHER INFORMATION: ELP tetrapeptide

<400> SEQUENCE: 2

Ile Pro Gly Gly
1

<210> SEQ ID NO 3
<211> LENGTH: 5
<212> TYPE: PRT
<213> ORGANISM: Artificial Sequence
<220> FEATURE:
<223> OTHER INFORMATION: ELP pentapeptide
<220> FEATURE:
<221> NAME/KEY: MISC_FEATURE
<222> LOCATION: (4)..(4)
<223> OTHER INFORMATION: Xaa may be any natural or non-natural amino
      acid residue, and where Xaa optionally varies among polymeric or
      oligomeric repeats

<400> SEQUENCE: 3

Val Pro Gly Xaa Gly
1               5

<210> SEQ ID NO 4
<211> LENGTH: 5
<212> TYPE: PRT
<213> ORGANISM: Artificial Sequence
<220> FEATURE:
<223> OTHER INFORMATION: ELP pentapeptide

<400> SEQUENCE: 4

Ala Val Gly Val Pro
1               5

<210> SEQ ID NO 5
<211> LENGTH: 5
<212> TYPE: PRT
<213> ORGANISM: Artificial Sequence
<220> FEATURE:
<223> OTHER INFORMATION: ELP pentapeptide
<220> FEATURE:
<221> NAME/KEY: MISC_FEATURE
<222> LOCATION: (4)..(4)
<223> OTHER INFORMATION: Xaa may be any natural or non-natural amino
      acid residue, and where Xaa optionally varies among polymeric or
```

```
                       oligomeric repeats

<400> SEQUENCE: 5

Ile Pro Gly Xaa Gly
1               5

<210> SEQ ID NO 6
<211> LENGTH: 5
<212> TYPE: PRT
<213> ORGANISM: Artificial Sequence
<220> FEATURE:
<223> OTHER INFORMATION: ELP pentapeptide

<400> SEQUENCE: 6

Ile Pro Gly Val Gly
1               5

<210> SEQ ID NO 7
<211> LENGTH: 5
<212> TYPE: PRT
<213> ORGANISM: Artificial Sequence
<220> FEATURE:
<223> OTHER INFORMATION: ELP pentapeptide
<220> FEATURE:
<221> NAME/KEY: misc_feature
<222> LOCATION: (4)..(4)
<223> OTHER INFORMATION: Xaa may be any natural or non-natural amino
      acid residue, and where Xaa optionally varies among polymeric or
      oligomeric repeats

<400> SEQUENCE: 7

Leu Pro Gly Xaa Gly
1               5

<210> SEQ ID NO 8
<211> LENGTH: 5
<212> TYPE: PRT
<213> ORGANISM: Artificial Sequence
<220> FEATURE:
<223> OTHER INFORMATION: ELP pentapeptide

<400> SEQUENCE: 8

Leu Pro Gly Val Gly
1               5

<210> SEQ ID NO 9
<211> LENGTH: 6
<212> TYPE: PRT
<213> ORGANISM: Artificial Sequence
<220> FEATURE:
<223> OTHER INFORMATION: ELP hexapeptide

<400> SEQUENCE: 9

Val Ala Pro Gly Val Gly
1               5

<210> SEQ ID NO 10
<211> LENGTH: 8
<212> TYPE: PRT
<213> ORGANISM: Artificial Sequence
<220> FEATURE:
<223> OTHER INFORMATION: ELP octapeptide

<400> SEQUENCE: 10

Gly Val Gly Val Pro Gly Val Gly
1               5
```

```
<210> SEQ ID NO 11
<211> LENGTH: 9
<212> TYPE: PRT
<213> ORGANISM: Artificial Sequence
<220> FEATURE:
<223> OTHER INFORMATION: ELP nonapeptide

<400> SEQUENCE: 11

Val Pro Gly Phe Gly Val Gly Ala Gly
1               5

<210> SEQ ID NO 12
<211> LENGTH: 9
<212> TYPE: PRT
<213> ORGANISM: Artificial Sequence
<220> FEATURE:
<223> OTHER INFORMATION: ELP nonapeptide

<400> SEQUENCE: 12

Val Pro Gly Val Gly Val Pro Gly Gly
1               5

<210> SEQ ID NO 13
<211> LENGTH: 28
<212> TYPE: PRT
<213> ORGANISM: Homo sapiens

<400> SEQUENCE: 13

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 14
<211> LENGTH: 634
<212> TYPE: PRT
<213> ORGANISM: Artificial Sequence
<220> FEATURE:
<223> OTHER INFORMATION: M-VIP ELP1-120

<400> SEQUENCE: 14

Met His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn Val Pro Gly
            20                  25                  30

Val Gly Val Pro Gly Val Gly Val Pro Gly Gly Val Pro Gly Ala
        35                  40                  45

Gly Val Pro Gly Val Gly Val Pro Gly Val Gly Val Pro Gly Val Gly
        50                  55                  60

Val Pro Gly Gly Val Pro Gly Ala Gly Val Pro Gly Gly Val
65                  70                  75                  80

Pro Gly Val Gly Val Pro Gly Val Gly Val Pro Gly Gly Val Pro
                85                  90                  95

Gly Ala Gly Val Pro Gly Val Gly Val Pro Gly Val Gly Val Pro Gly
                100                 105                 110

Val Gly Val Pro Gly Gly Val Pro Gly Ala Gly Val Pro Gly Gly
            115                 120                 125

Gly Val Pro Gly Val Gly Val Pro Gly Val Gly Val Pro Gly Gly Gly
            130                 135                 140

Val Pro Gly Ala Gly Val Pro Gly Val Gly Val Pro Gly Val Gly Val
145                 150                 155                 160
```

Pro Gly Val Gly Val Pro Gly Gly Val Pro Gly Ala Gly Val Pro
            165                 170                 175

Gly Gly Gly Val Pro Gly Val Gly Val Pro Gly Val Gly Val Pro Gly
        180                 185                 190

Gly Gly Val Pro Gly Ala Gly Val Pro Gly Val Gly Val Pro Gly Val
    195                 200                 205

Gly Val Pro Gly Val Gly Val Pro Gly Gly Gly Val Pro Gly Ala Gly
210                 215                 220

Val Pro Gly Gly Gly Val Pro Gly Val Gly Val Pro Gly Val Gly Val
225                 230                 235                 240

Pro Gly Gly Gly Val Pro Gly Ala Gly Val Pro Gly Val Gly Val Pro
                245                 250                 255

Gly Val Gly Val Pro Gly Val Gly Val Pro Gly Gly Gly Val Pro Gly
            260                 265                 270

Ala Gly Val Pro Gly Gly Gly Val Pro Gly Val Gly Val Pro Gly Val
        275                 280                 285

Gly Val Pro Gly Gly Gly Val Pro Gly Ala Gly Val Pro Gly Val Gly
    290                 295                 300

Val Pro Gly Val Gly Val Pro Gly Val Gly Val Pro Gly Gly Gly Val
305                 310                 315                 320

Pro Gly Ala Gly Val Pro Gly Gly Gly Val Pro Gly Val Gly Val Pro
                325                 330                 335

Gly Val Gly Val Pro Gly Gly Gly Val Pro Gly Ala Gly Val Pro Gly
            340                 345                 350

Val Gly Val Pro Gly Val Gly Val Pro Gly Val Gly Val Pro Gly Gly
        355                 360                 365

Gly Val Pro Gly Ala Gly Val Pro Gly Gly Gly Val Pro Gly Val Gly
    370                 375                 380

Val Pro Gly Val Gly Val Pro Gly Gly Gly Val Pro Gly Ala Gly Val
385                 390                 395                 400

Pro Gly Val Gly Val Pro Gly Val Gly Val Pro Gly Val Gly Val Pro
                405                 410                 415

Gly Gly Gly Val Pro Gly Ala Gly Val Pro Gly Gly Gly Val Pro Gly
            420                 425                 430

Val Gly Val Pro Gly Val Gly Val Pro Gly Gly Gly Val Pro Gly Ala
        435                 440                 445

Gly Val Pro Gly Val Gly Val Pro Gly Val Gly Val Pro Gly Val Gly
    450                 455                 460

Val Pro Gly Gly Gly Val Pro Gly Ala Gly Val Pro Gly Gly Gly Val
465                 470                 475                 480

Pro Gly Val Gly Val Pro Gly Val Gly Val Pro Gly Gly Gly Val Pro
                485                 490                 495

Gly Ala Gly Val Pro Gly Val Gly Val Pro Gly Val Gly Val Pro Gly
            500                 505                 510

Val Gly Val Pro Gly Gly Gly Val Pro Gly Ala Gly Val Pro Gly Gly
        515                 520                 525

Gly Val Pro Gly Val Gly Val Pro Gly Val Gly Val Pro Gly Gly Gly
    530                 535                 540

Val Pro Gly Ala Gly Val Pro Gly Val Gly Val Pro Gly Val Gly Val
545                 550                 555                 560

Pro Gly Val Gly Val Pro Gly Gly Gly Val Pro Gly Ala Gly Val Pro
                565                 570                 575

Gly Gly Gly Val Pro Gly Val Gly Val Pro Gly Val Gly Val Pro Gly

```
                580             585             590
Gly Gly Val Pro Gly Ala Gly Val Pro Gly Val Gly Val Pro Gly Val
                595             600             605

Gly Val Pro Gly Val Gly Val Pro Gly Gly Gly Val Pro Gly Ala Gly
            610             615             620

Val Pro Gly Gly Gly Val Pro Gly Trp Pro
625             630

<210> SEQ ID NO 15
<211> LENGTH: 636
<212> TYPE: PRT
<213> ORGANISM: Artificial Sequence
<220> FEATURE:
<223> OTHER INFORMATION: MAA-VIP ELP1-120

<400> SEQUENCE: 15

Met Ala Ala His Ser Asp Ala Val Phe Thr Asp Asn Tyr Thr Arg Leu
1               5                   10                  15

Arg Lys Gln Met Ala Val Lys Lys Tyr Leu Asn Ser Ile Leu Asn Val
            20                  25                  30

Pro Gly Val Gly Val Pro Gly Val Gly Val Pro Gly Gly Gly Val Pro
        35                  40                  45

Gly Ala Gly Val Pro Gly Val Gly Val Pro Gly Val Gly Val Pro Gly
    50                  55                  60

Val Gly Val Pro Gly Gly Gly Val Pro Gly Ala Gly Val Pro Gly Gly
65                  70                  75                  80

Gly Val Pro Gly Val Gly Val Pro Gly Val Gly Val Pro Gly Gly Gly
                85                  90                  95

Val Pro Gly Ala Gly Val Pro Gly Val Gly Val Pro Gly Val Gly Val
                100                 105                 110

Pro Gly Val Gly Val Pro Gly Gly Gly Val Pro Gly Ala Gly Val Pro
        115                 120                 125

Gly Gly Gly Val Pro Gly Val Gly Val Pro Gly Val Gly Val Pro Gly
    130                 135                 140

Gly Gly Val Pro Gly Ala Gly Val Pro Gly Val Gly Val Pro Gly Val
145                 150                 155                 160

Gly Val Pro Gly Val Gly Val Pro Gly Gly Gly Val Pro Gly Ala Gly
                165                 170                 175

Val Pro Gly Gly Gly Val Pro Gly Val Gly Val Pro Gly Val Gly Val
            180                 185                 190

Pro Gly Gly Gly Val Pro Gly Ala Gly Val Pro Gly Val Gly Val Pro
        195                 200                 205

Gly Val Gly Val Pro Gly Val Gly Val Pro Gly Gly Gly Val Pro Gly
    210                 215                 220

Ala Gly Val Pro Gly Gly Gly Val Pro Gly Val Gly Val Pro Gly Val
225                 230                 235                 240

Gly Val Pro Gly Gly Gly Val Pro Gly Ala Gly Val Pro Gly Val Gly
                245                 250                 255

Val Pro Gly Val Gly Val Pro Gly Val Gly Val Pro Gly Gly Gly Val
            260                 265                 270

Pro Gly Ala Gly Val Pro Gly Gly Gly Val Pro Gly Val Gly Val Pro
        275                 280                 285

Gly Val Gly Val Pro Gly Gly Gly Val Pro Gly Ala Gly Val Pro Gly
    290                 295                 300

Val Gly Val Pro Gly Val Gly Val Pro Gly Val Gly Val Pro Gly Gly
```

```
                305                 310                 315                 320
Gly Val Pro Gly Ala Gly Val Pro Gly Gly Val Pro Val Gly
                    325                 330                 335
Val Pro Gly Val Gly Val Pro Gly Gly Val Pro Gly Ala Gly Val
                340                 345                 350
Pro Gly Val Gly Val Pro Gly Val Gly Val Pro Gly Val Gly Val Pro
                355                 360                 365
Gly Gly Gly Val Pro Gly Ala Gly Val Pro Gly Gly Val Pro Gly
            370                 375                 380
Val Gly Val Pro Gly Val Gly Val Pro Gly Gly Val Pro Gly Ala
385                 390                 395                 400
Gly Val Pro Gly Val Gly Val Pro Gly Val Gly Val Pro Gly Val Gly
                405                 410                 415
Val Pro Gly Gly Gly Val Pro Gly Ala Gly Val Pro Gly Gly Val
                    420                 425                 430
Pro Gly Val Gly Val Pro Gly Val Gly Val Pro Gly Gly Gly Val Pro
                435                 440                 445
Gly Ala Gly Val Pro Gly Val Gly Val Pro Gly Val Gly Val Pro Gly
            450                 455                 460
Val Gly Val Pro Gly Gly Gly Val Pro Gly Ala Gly Val Pro Gly Gly
465                 470                 475                 480
Gly Val Pro Gly Val Gly Val Pro Gly Val Gly Val Pro Gly Gly Gly
                    485                 490                 495
Val Pro Gly Ala Gly Val Pro Gly Val Gly Val Pro Gly Val Gly Val
                500                 505                 510
Pro Gly Val Gly Val Pro Gly Gly Val Pro Gly Ala Gly Val Pro
                515                 520                 525
Gly Gly Gly Val Pro Gly Val Gly Val Pro Gly Val Gly Val Pro Gly
            530                 535                 540
Gly Gly Val Pro Gly Ala Gly Val Pro Gly Val Gly Val Pro Gly Val
545                 550                 555                 560
Gly Val Pro Gly Val Gly Val Pro Gly Gly Gly Val Pro Gly Ala Gly
                    565                 570                 575
Val Pro Gly Gly Gly Val Pro Gly Val Gly Val Pro Gly Val Gly Val
                580                 585                 590
Pro Gly Gly Gly Val Pro Gly Ala Gly Val Pro Gly Val Gly Val Pro
                595                 600                 605
Gly Val Gly Val Pro Gly Val Gly Val Pro Gly Gly Gly Val Pro Gly
            610                 615                 620
Ala Gly Val Pro Gly Gly Gly Val Pro Gly Trp Pro
625                 630                 635

<210> SEQ ID NO 16
<211> LENGTH: 93
<212> TYPE: DNA
<213> ORGANISM: Homo sapiens

<400> SEQUENCE: 16
atggcggccc actctgacgc tgttttcact gacaactaca ctcgtctgcg taaacagatg      60
gctgttaaaa agtacctgaa ctctatcctg aac                                   93

<210> SEQ ID NO 17
<211> LENGTH: 29
<212> TYPE: PRT
<213> ORGANISM: Artificial Sequence
```

```
<220> FEATURE:
<223> OTHER INFORMATION: VIP : MODIFIED PROTEIN PB1046

<400> SEQUENCE: 17

Met His Ser Asp Ala Val Phe Thr Asp Asn Tyr Thr Arg Leu Arg Lys
1               5                   10                  15

Gln Met Ala Val Lys Lys Tyr Leu Asn Ser Ile Leu Asn
            20                  25

<210> SEQ ID NO 18
<211> LENGTH: 31
<212> TYPE: PRT
<213> ORGANISM: Artificial Sequence
<220> FEATURE:
<223> OTHER INFORMATION: VIP : MODIFIED PROTEIN PB1047

<400> SEQUENCE: 18

Met Ala Ala His Ser Asp Ala Val Phe Thr Asp Asn Tyr Thr Arg Leu
1               5                   10                  15

Arg Lys Gln Met Ala Val Lys Lys Tyr Leu Asn Ser Ile Leu Asn
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: VIP : MODIFIED PROTEIN PB1064

<400> SEQUENCE: 19

Met Ala Ala His Gly Asp Ala Val Phe Thr Asp Asn Tyr Thr Arg Leu
1               5                   10                  15

Arg Lys Gln Met Ala Val Lys Lys Tyr Leu Asn Ser Ile Leu Asn
            20                  25                  30

<210> SEQ ID NO 20
<211> LENGTH: 51
<212> TYPE: PRT
<213> ORGANISM: Artificial Sequence
<220> FEATURE:
<223> OTHER INFORMATION: VIP : MODIFIED PROTEIN PB1056

<400> SEQUENCE: 20

Met Ala Ala His Ser Asp Ala Val Phe Thr Asp Asn Tyr Thr Arg Leu
1               5                   10                  15

Arg Lys Gln Met Ala Val Lys Lys Tyr Leu Asn Ser Ile Leu Asn Val
            20                  25                  30

Pro Gly Glu Gly Val Pro Gly Asp Gly Val Pro Gly Glu Gly Val Pro
        35                  40                  45

Gly Asp Gly
    50

<210> SEQ ID NO 21
<211> LENGTH: 28
<212> TYPE: PRT
<213> ORGANISM: Artificial Sequence
<220> FEATURE:
<223> OTHER INFORMATION: VIP : MODIFIED PROTEIN

<400> SEQUENCE: 21

His Ser Asp Ala Val Phe Thr Asp Asn Tyr Thr Arg Leu Arg Lys Gln
1               5                   10                  15

Leu Ala Val Lys Lys Tyr Leu Asn Ser Ile Leu Asn
```

```
            20                  25

<210> SEQ ID NO 22
<211> LENGTH: 28
<212> TYPE: PRT
<213> ORGANISM: Artificial Sequence
<220> FEATURE:
<223> OTHER INFORMATION: VIP : MODIFIED PROTEIN

<400> SEQUENCE: 22

His Ser Asp Ala Val Phe Thr Asp Asn Tyr Thr Arg Leu Arg Arg Gln
1               5                   10                  15

Met Ala Val Arg Arg Tyr Leu Asn Ser Ile Leu Asn
            20                  25

<210> SEQ ID NO 23
<211> LENGTH: 28
<212> TYPE: PRT
<213> ORGANISM: Artificial Sequence
<220> FEATURE:
<223> OTHER INFORMATION: VIP : MODIFIED PROTEIN

<400> SEQUENCE: 23

His Ser Asp Ala Val Phe Thr Asp Asn Tyr Thr Arg Leu Arg Lys Gln
1               5                   10                  15

Met Ala Val Lys Lys Tyr Leu Ala Ala Ile Leu Asn
            20                  25

<210> SEQ ID NO 24
<211> LENGTH: 31
<212> TYPE: PRT
<213> ORGANISM: Artificial Sequence
<220> FEATURE:
<223> OTHER INFORMATION: VIP : MODIFIED PROTEIN
<220> FEATURE:
<221> NAME/KEY: MISC_FEATURE
<222> LOCATION: (5)..(5)
<223> OTHER INFORMATION: Xaa may be Ser or Gly

<400> SEQUENCE: 24

Met Ala Ala His Xaa Asp Ala Val Phe Thr Asp Asn Tyr Thr Arg Leu
1               5                   10                  15

Arg Lys Gln Leu Ala Val Lys Lys Tyr Leu Asn Ser Ile Leu Asn
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: VIP : MODIFIED PROTEIN
<220> FEATURE:
<221> NAME/KEY: MISC_FEATURE
<222> LOCATION: (5)..(5)
<223> OTHER INFORMATION: Xaa may be Ser or Gly

<400> SEQUENCE: 25

Met Ala Ala His Xaa Asp Ala Val Phe Thr Asp Asn Tyr Thr Arg Leu
1               5                   10                  15

Arg Lys Gln Leu Ala Val Lys Lys Tyr Leu Ala Ala Ile Leu Asn
            20                  25                  30

<210> SEQ ID NO 26
<211> LENGTH: 31
<212> TYPE: PRT
<213> ORGANISM: Artificial Sequence
```

```
<220> FEATURE:
<223> OTHER INFORMATION: VIP : MODIFIED PROTEIN
<220> FEATURE:
<221> NAME/KEY: MISC_FEATURE
<222> LOCATION: (5)..(5)
<223> OTHER INFORMATION: Xaa may be Ser or Gly

<400> SEQUENCE: 26

Met Ala Ala His Xaa Asp Ala Val Phe Thr Asp Asn Tyr Thr Arg Leu
1               5                   10                  15

Arg Arg Gln Leu Ala Val Arg Arg Tyr Leu Asn Ser Ile Leu Asn
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: VIP : MODIFIED PROTEIN
<220> FEATURE:
<221> NAME/KEY: MISC_FEATURE
<222> LOCATION: (5)..(5)
<223> OTHER INFORMATION: Xaa may be Ser or Gly

<400> SEQUENCE: 27

Met Ala Ala His Xaa Asp Ala Val Phe Thr Asp Asn Tyr Thr Arg Leu
1               5                   10                  15

Arg Arg Gln Leu Ala Val Arg Arg Tyr Leu Ala Ala Ile Leu Asn
            20                  25                  30

<210> SEQ ID NO 28
<211> LENGTH: 27
<212> TYPE: PRT
<213> ORGANISM: UNKNOWN
<220> FEATURE:
<223> OTHER INFORMATION: PACAP-27 : NATIVE PROTEIN

<400> SEQUENCE: 28

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 29
<211> LENGTH: 38
<212> TYPE: PRT
<213> ORGANISM: UNKNOWN
<220> FEATURE:
<223> OTHER INFORMATION: PACAP-38 : NATIVE PROTEIN

<400> SEQUENCE: 29

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 30
<211> LENGTH: 41
<212> TYPE: PRT
<213> ORGANISM: Artificial Sequence
<220> FEATURE:
<223> OTHER INFORMATION: PACAP  : MODIFIED PROTEIN

<400> SEQUENCE: 30
```

```
Met Ala Ala His Gly Asp Gly Ile Phe Thr Asp Ser Tyr Ser Arg Tyr
1               5                   10                  15

Arg Arg Gln Leu Ala Val Arg Tyr Leu Ala Ala Val Leu Gly Val
            20                  25                  30

Pro Gly Glu Gly Val Pro Gly Asp Gly
        35                  40

<210> SEQ ID NO 31
<211> LENGTH: 60
<212> TYPE: DNA
<213> ORGANISM: Artificial Sequence
<220> FEATURE:
<223> OTHER INFORMATION: P0045 : PRIMER

<400> SEQUENCE: 31
aattctctag aataatttt gtttaacttt aagaaggaga tatacatatg cactctgacg       60

<210> SEQ ID NO 32
<211> LENGTH: 76
<212> TYPE: DNA
<213> ORGANISM: Artificial Sequence
<220> FEATURE:
<223> OTHER INFORMATION: P0048 : PRIMER

<400> SEQUENCE: 32
gtagttgtca gtgaaaacag cgtcagagtg catatgtata tctccttctt aaagttaaac      60
aaaattattt ctagag                                                     76

<210> SEQ ID NO 33
<211> LENGTH: 78
<212> TYPE: DNA
<213> ORGANISM: Artificial Sequence
<220> FEATURE:
<223> OTHER INFORMATION: P0064: PRIMER

<400> SEQUENCE: 33
ctgttttcac tgacaactac actcgtctgc gtaaacagat ggctgttaaa aagtacctga      60
actctatcct gaacgtac                                                   78

<210> SEQ ID NO 34
<211> LENGTH: 54
<212> TYPE: DNA
<213> ORGANISM: Artificial Sequence
<220> FEATURE:
<223> OTHER INFORMATION: P0065 : PRIMER

<400> SEQUENCE: 34
gttcaggata gagttcaggt acttttaac agccatctgt ttacgcagac gagt             54

<210> SEQ ID NO 35
<211> LENGTH: 60
<212> TYPE: DNA
<213> ORGANISM: Artificial Sequence
<220> FEATURE:
<223> OTHER INFORMATION: P0066 : PRIMER

<400> SEQUENCE: 35
ctagaaataa ttttgtttaa ctttaagaag gagatataca tatggcggcc cactctgacg      60

<210> SEQ ID NO 36
<211> LENGTH: 76
<212> TYPE: DNA
<213> ORGANISM: Artificial Sequence
```

<220> FEATURE:
<223> OTHER INFORMATION: P0067 : PRIMER

<400> SEQUENCE: 36

```
gtagttgtca gtgaaaacag cgtcagagtg ggccgccata tgtatatctc cttcttaaag    60
ttaaacaaaa ttattt                                                     76
```

<210> SEQ ID NO 37
<211> LENGTH: 97
<212> TYPE: DNA
<213> ORGANISM: Artificial Sequence
<220> FEATURE:
<223> OTHER INFORMATION: P0068 : PRIMER

<400> SEQUENCE: 37

```
tggccgcact ctgacgctgt tttcactgac aactacactc gtctgcgtaa acagatggct    60
gttaaaaagt acctgaactc tatcctgaac tgataag                              97
```

<210> SEQ ID NO 38
<211> LENGTH: 104
<212> TYPE: DNA
<213> ORGANISM: Artificial Sequence
<220> FEATURE:
<223> OTHER INFORMATION: P0069 : PRIMER

<400> SEQUENCE: 38

```
ctagcttatc agttcaggat agagttcagg tactttttaa cagccatctg tttacgcaga    60
cgagtgtagt tgtcagtgaa aacagcgtca gagtgcggcc agcc                     104
```

<210> SEQ ID NO 39
<211> LENGTH: 240
<212> TYPE: DNA
<213> ORGANISM: Artificial Sequence
<220> FEATURE:
<223> OTHER INFORMATION: pPB1046-mVIP-ELP 1-120 fusion sequence

<400> SEQUENCE: 39

```
taatacgact cactataggg gaattgtgag cggataacaa ttcccctcta gaaataattt    60
tgtttaactt taagaaggag atatacatat gcactctgac gctgttttca ctgacaacta   120
cactcgtctg cgtaaacaga tggctgttaa aaagtacctg aactctatcc tgaacgtacc   180
gggcgtgggt gttccgggcg tgggtgttcc gggtggcggt gtgccgggcg caggtgttcc   240
```

<210> SEQ ID NO 40
<211> LENGTH: 50
<212> TYPE: PRT
<213> ORGANISM: Artificial Sequence
<220> FEATURE:
<223> OTHER INFORMATION: mVIP-ELP 1-120 fusion sequence

<400> SEQUENCE: 40

```
Met His Ser Asp Ala Val Phe Thr Asp Asn Tyr Thr Arg Leu Arg Lys
 1               5                  10                  15

Gln Met Ala Val Lys Lys Tyr Leu Asn Ser Ile Leu Asn Val Pro Gly
             20                  25                  30

Val Gly Val Pro Gly Val Gly Val Pro Gly Gly Gly Val Pro Gly Ala
         35                  40                  45

Gly Val
     50
```

<210> SEQ ID NO 41

-continued

```
<211> LENGTH: 240
<212> TYPE: DNA
<213> ORGANISM: Artificial Sequence
<220> FEATURE:
<223> OTHER INFORMATION: pPB1047 mVIP-ELP 1-120 fusion sequence

<400> SEQUENCE: 41
taatacgact cactataggg gaattgtgag cggataacaa ttcccctcta gaaataattt      60
tgtttaactt taagaaggag atatacatat ggcggcccac tctgacgctg ttttcactga    120
caactacact cgtctgcgta aacagatggc tgttaaaaag tacctgaact ctatcctgaa    180
cgtaccgggc gtgggtgttc cgggcgtggg tgttccgggt ggcggtgtgc cgggcgcagg    240

<210> SEQ ID NO 42
<211> LENGTH: 49
<212> TYPE: PRT
<213> ORGANISM: Artificial Sequence
<220> FEATURE:
<223> OTHER INFORMATION: mVIP-ELP 1-120 fusion sequence

<400> SEQUENCE: 42

Met Ala Ala His Ser Asp Ala Val Phe Thr Asp Asn Tyr Thr Arg Leu
1               5                   10                  15

Arg Lys Gln Met Ala Val Lys Lys Tyr Leu Asn Ser Ile Leu Val Pro
            20                  25                  30

Gly Val Gly Val Pro Gly Val Gly Val Pro Gly Gly Gly Val Pro Gly
        35                  40                  45

Ala

<210> SEQ ID NO 43
<211> LENGTH: 180
<212> TYPE: DNA
<213> ORGANISM: Artificial Sequence
<220> FEATURE:
<223> OTHER INFORMATION: pPB1048 ELP 1-120-VIP fusion sequence

<400> SEQUENCE: 43
tgttccgggt gcaggcgttc cgggtggcgg tgtgccgggc tggccgcact ctgacgctgt     60
tttcactgac aactacactc gtctgcgtaa acagatggc gttaaaaagt acctgaactc    120
tatcctgaac tgataagcta gcatgactgg tggacagcaa atgggtcgga tccgaattcg    180

<210> SEQ ID NO 44
<211> LENGTH: 44
<212> TYPE: PRT
<213> ORGANISM: Artificial Sequence
<220> FEATURE:
<223> OTHER INFORMATION: ELP 1-120-VIP fusion sequence

<400> SEQUENCE: 44

Gly Val Pro Gly Ala Gly Val Pro Gly Gly Val Pro Gly Trp Pro
1               5                   10                  15

His Ser Asp Ala Val Phe Thr Asp Asn Tyr Thr Arg Leu Arg Lys Gln
            20                  25                  30

Met Ala Val Lys Lys Tyr Leu Asn Ser Ile Leu Asn
        35                  40

<210> SEQ ID NO 45
<211> LENGTH: 5
<212> TYPE: PRT
<213> ORGANISM: Artificial Sequence
<220> FEATURE:
<223> OTHER INFORMATION: Modified VIP N-terminus
```

<400> SEQUENCE: 45

Met Ala Ala His Gly
1               5

<210> SEQ ID NO 46
<211> LENGTH: 5
<212> TYPE: PRT
<213> ORGANISM: Artificial Sequence
<220> FEATURE:
<223> OTHER INFORMATION: Modified VIP N-terminus

<400> SEQUENCE: 46

Met Ala Ala His Ser
1               5

<210> SEQ ID NO 47
<211> LENGTH: 4
<212> TYPE: PRT
<213> ORGANISM: Artificial Sequence
<220> FEATURE:
<223> OTHER INFORMATION: Peptide spacer sequence

<400> SEQUENCE: 47

Gly Phe Leu Gly
1

<210> SEQ ID NO 48
<211> LENGTH: 8135
<212> TYPE: DNA
<213> ORGANISM: Artificial Sequence
<220> FEATURE:
<223> OTHER INFORMATION: pPB1120

<400> SEQUENCE: 48
taatacgact cactataggg gaattgtgag cggataacaa ttcccctcta gaaataattt      60
tgtttaactt taagaaggag atatacatat ggagaacctg tatttccaac actctgacgc     120
tgttttcact gacaactaca ctcgtctgcg taaacagatg gctgttaaaa agtacctgaa     180
ctctatcctg aacgtaccgg gcgtgggtgt tccgggcgtg ggtgttccgg gtggcggtgt     240
gccgggcgca ggtgttcctg gtgtaggtgt gccgggtgtt ggtgtgccgg gtgttggtgt     300
accaggtggc ggtgttccgg gtgcaggcgt tccgggtggc ggtgtgccgg gcgtgggtgt     360
tccgggcgtg ggtgttccgg gtggcggtgt gccgggcgca ggtgttcctg gtgtaggtgt     420
gccgggtgtt ggtgtgccgg gtgttggtgt accaggtggc ggtgttccgg gtgcaggcgt     480
tccgggtggc ggtgtgccgg gcgtgggtgt tccgggcgtg ggtgttccgg gtggcggtgt     540
gccgggcgca ggtgttcctg gtgtaggtgt gccgggtgtt ggtgtgccgg gtgttggtgt     600
accaggtggc ggtgttccgg gtgcaggcgt tccgggtggc ggtgtgccgg gcgtgggtgt     660
tccgggcgtg ggtgttccgg gtggcggtgt gccgggcgca ggtgttcctg gtgtaggtgt     720
gccgggtgtt ggtgtgccgg gtgttggtgt accaggtggc ggtgttccgg gtgcaggcgt     780
tccgggtggc ggtgtgccgg gcgtgggtgt tccgggcgtg ggtgttccgg gtggcggtgt     840
gccgggcgca ggtgttcctg gtgtaggtgt gccgggtgtt ggtgtgccgg gtgttggtgt     900
accaggtggc ggtgttccgg gtgcaggcgt tccgggtggc ggtgtgccgg gcgtgggtgt     960
tccgggcgtg ggtgttccgg gtggcggtgt gccgggcgca ggtgttcctg gtgtaggtgt    1020
gccgggtgtt ggtgtgccgg gtgttggtgt accaggtggc ggtgttccgg gtgcaggcgt    1080
tccgggtggc ggtgtgccgg gcgtgggtgt tccgggcgtg ggtgttccgg gtggcggtgt    1140

```
gccgggcgca ggtgttcctg gtgtaggtgt gccgggtgtt ggtgtgccgg gtgttggtgt    1200
accaggtggc ggtgttccgg gtgcaggcgt tccgggtggc ggtgtgccgg gcgtgggtgt    1260
tccgggcgtg ggtgttccgg gtggcggtgt gccgggcgca ggtgttcctg gtgtaggtgt    1320
gccgggtgtt ggtgtgccgg gtgttggtgt accaggtggc ggtgttccgg gtgcaggcgt    1380
tccgggtggc ggtgtgccgg gcgtgggtgt tccgggcgtg ggtgttccgg gtggcggtgt    1440
gccgggcgca ggtgttcctg gtgtaggtgt gccgggtgtt ggtgtgccgg gtgttggtgt    1500
accaggtggc ggtgttccgg gtgcaggcgt tccgggtggc ggtgtgccgg gcgtgggtgt    1560
tccgggcgtg ggtgttccgg gtggcggtgt gccgggcgca ggtgttcctg gtgtaggtgt    1620
gccgggtgtt ggtgtgccgg gtgttggtgt accaggtggc ggtgttccgg gtgcaggcgt    1680
tccgggtggc ggtgtgccgg gcgtgggtgt tccgggcgtg ggtgttccgg gtggcggtgt    1740
gccgggcgca ggtgttcctg gtgtaggtgt gccgggtgtt ggtgtgccgg gtgttggtgt    1800
accaggtggc ggtgttccgg gtgcaggcgt tccgggtggc ggtgtgccgg gcgtgggtgt    1860
tccgggcgtg ggtgttccgg gtggcggtgt gccgggcgca ggtgttcctg gtgtaggtgt    1920
gccgggtgtt ggtgtgccgg gtgttggtgt accaggtggc ggtgttccgg gtgcaggcgt    1980
tccgggtggc ggtgtgccgg gctggccgtg ataagctagc atgactggtg gacagcaaat    2040
gggtcggatc cgaattcgag ctccgtcgag caccaccacc accaccacca ccactaattg    2100
attaatacct aggctgctaa acaaagcccg aaaggaagct gagttggctg ctgccaccgc    2160
tgagcaataa ctagcataac cccttggggc ctctaaacgg gtcttgaggg gttttttgct    2220
gaaaggagga actatatccg gattggcgaa tgggacgcgc cctgtagcgg cgcattaagc    2280
gcggcgggtg tggtggttac gcgcagcgtg accgctacac ttgccagcgc cctagcgccc    2340
gctcctttcg ctttcttccc ttcctttctc gccacgttcg ccggctttcc ccgtcaagct    2400
ctaaatcggg ggctcccttt agggttccga tttagtgctt tacggcacct cgaccccaaa    2460
aaacttgatt agggtgatgg ttcacgtagt gggccatcgc cctgatagac ggtttttcgc    2520
cctttgacgt tggagtccac gttctttaat agtggactct tgttccaaac tggaacaaca    2580
ctcaacccta tctcggtcta ttcttttgat ttataaggga ttttgccgat ttcggcctat    2640
tggttaaaaa atgagctgat ttaacaaaaa tttaacgcga attttaacaa aatattaacg    2700
tttacaattt caggtggcac ttttcgggga aatgtgcgcg gaaccccctat ttgtttattt    2760 ttctaaatac attcaaatat gtatccgctc atgaattaat tcttagaaaa actcatcgag    2820
catcaaatga aactgcaatt tattcatatc aggattatca ataccatatt tttgaaaaag    2880
ccgtttctgt aatgaaggag aaaactcacc gaggcagttc cataggatgg caagatcctg    2940
gtatcggtct gcgattccga ctcgtccaac atcaatacaa cctattaatt tcccctcgtc    3000
aaaaataagg ttatcaagtg agaaatcacc atgagtgacg actgaatccg gtgagaatgg    3060
caaaagttta tgcatttctt tccagacttg ttcaacaggc cagccattac gctcgtcatc    3120
aaaatcactc gcatcaacca accgttatt cattcgtgat tgcgcctgag cgagacgaaa    3180
tacgcgatcg ctgttaaaag gacaattaca acaggaatc gaatgcaacc ggcgcaggaa    3240
cactgccagc gcatcaacaa tattttcacc tgaatcagga tattcttcta atacctggaa    3300
tgctgttttc ccggggatcg cagtggtgag taaccatgca tcatcaggag tacggataaa    3360
atgcttgatg gtcggaagag gcataaattc cgtcagccag tttagtctga ccatctcatc    3420
tgtaacatca ttggcaacgc tacctttgcc atgtttcaga aacaactctg gcgcatcggg    3480
```

```
cttcccatac aatcgataga ttgtcgcacc tgattgcccg acattatcgc gagcccattt   3540
atacccatat aaatcagcat ccatgttgga atttaatcgc ggcctagagc aagacgtttc   3600
ccgttgaata tggctcataa caccccttgt attactgttt atgtaagcag acagttttat   3660
tgttcatgac caaatccct taacgtgagt tttcgttcca ctgagcgtca gaccccgtag   3720
aaaagatcaa aggatcttct tgagatcctt ttttctgcg cgtaatctgc tgcttgcaaa   3780
caaaaaaacc accgctacca gcggtggttt gtttgccgga tcaagagcta ccaactcttt   3840
ttccgaaggt aactggcttc agcagagcgc agataccaaa tactgtcctt ctagtgtagc   3900
cgtagttagg ccaccacttc aagaactctg tagcaccgcc tacatacctc gctctgctaa   3960
tcctgttacc agtggctgct gccagtggcg ataagtcgtg tcttaccggg ttggactcaa   4020
gacgatagtt accggataag gcgcagcggt cgggctgaac ggggggttcg tgcacacagc   4080
ccagcttgga gcgaacgacc tacaccgaac tgagatacct acagcgtgag ctatgagaaa   4140
gcgccacgct tcccgaaggg agaaaggcgg acaggtatcc ggtaagcggc agggtcggaa   4200
caggagagcg cacgagggag cttccagggg gaaacgcctg gtatctttat agtcctgtcg   4260
ggtttcgcca cctctgactt gagcgtcgat ttttgtgatg ctcgtcaggg gggcggagcc   4320 tatgaaaaa cgccagcaac gcggcctttt tacggttcct ggccttttgc tggccttttg   4380
ctcacatgtt ctttcctgcg ttatcccctg attctgtgga taaccgtatt accgcctttg   4440
agtgagctga taccgctcgc cgcagccgaa cgaccgagcg cagcgagtca gtgagcgagg   4500
aagcggaaga gcgcctgatg cggtattttc tccttacgca tctgtgcggt atttcacacc   4560
gcatatatgg tgcactctca gtacaatctg ctctgatgcc gcatagttaa gccagtatac   4620
actccgctat cgctacgtga ctgggtcatg gctgcgcccc gacacccgcc aacacccgct   4680
gacgcgccct gacgggcttg tctgctcccg gcatccgctt acagacaagc tgtgaccgtc   4740
tccgggagct gcatgtgtca gaggttttca ccgtcatcac cgaaacgcgc gaggcagctg   4800
cggtaaagct catcagcgtg gtcgtgaagc gattcacaga tgtctgcctg ttcatccgcg   4860
tccagctcgt tgagtttctc cagaagcgtt aatgtctggc ttctgataaa gcgggccatg   4920
ttaagggcgg ttttttcctg tttggtcact gatgcctccg tgtaagggg atttctgttc   4980 atgggggtaa tgataccgat gaaacgagag aggatgctca cgatacgggt tactgatgat   5040
gaacatgccc ggttactgga acgttgtgag ggtaaacaac tggcggtatg gatgcggcgg   5100
gaccagagaa aaatcactca gggtcaatgc cagcgcttcg ttaatacaga tgtaggtgtt   5160
ccacagggta gccagcagca tcctgcgatg cagatccgga acataatggt gcagggcgct   5220
gacttccgcg tttccagact ttacgaaaca cggaaaccga agaccattca tgttgttgct   5280
caggtcgcag acgttttgca gcagcagtcg cttcacgttc gctcgcgtat cggtgattca   5340
ttctgctaac cagtaaggca accccgccag cctagccggg tcctcaacga caggagcacg   5400
atcatgctag tcatgccccg cgcccaccgg aaggagctga ctgggttgaa ggctctcaag   5460
ggcatcggtc gagatcccgg tgcctaatga gtgagctaac ttcacattaat tgcgttgcgc   5520 tcactgcccg ctttccagtc gggaaacctg tcgtgccagc tgcattaatg aatcggccaa   5580
cgcgcgggga gaggcggttt gcgtattggg cgccagggtg ttttttcttt tcaccagtga   5640
gacgggcaac agctgattgc ccttcaccgc ctggccctga gagagttgca gcaagcggtc   5700
cacgctggtt tgccccagca ggcgaaaatc ctgtttgatg gtggttaacg gcgggatata   5760
acatgagctg tcttcggtat cgtcgtatcc cactaccgag atgtccgcac caacgcgcag   5820
cccggactcg gtaatggcgc gcattgcgcc cagcgccatc tgatcgttgg caaccagcat   5880
```

```
cgcagtggga acgatgccct cattcagcat ttgcatggtt tgttgaaaac cggacatggc    5940
actccagtcg ccttcccgtt ccgctatcgg ctgaatttga ttgcgagtga gatatttatg    6000
ccagccagcc agacgcagac gcgccgagac agaacttaat gggcccgcta acagcgcgat    6060
ttgctggtga cccaatgcga ccagatgctc cacgcccagt cgcgtaccgt cttcatggga    6120
gaaataata ctgttgatgg gtgtctggtc agagacatca agaaataacg ccggaacatt      6180
agtgcaggca gcttccacag caatggcatc ctggtcatcc agcggatagt taatgatcag    6240
cccactgacg cgttgcgcga aagattgtg caccgccgct ttacaggctt cgacgccgct     6300
tcgttctacc atcgcacca ccacgctggc acccagttga tcggcgcgag atttaatcgc     6360
cgcgacaatt tgcgacggcg cgtgcagggc cagactggag gtggcaacgc caatcagcaa    6420
cgactgtttg cccgccagtt gttgtgccac gcggttggga atgtaattca gctccgccat    6480
cgccgcttcc actttttccc gcgttttcgc agaaacgtgg ctggcctggt tcaccacgcg    6540
ggaaacggtc tgataagaga caccggcata ctctgcgaca tcgtataacg ttactggttt    6600
cacattcacc accctgaatt gactctcttc cgggcgctat catgccatac cgcgaaaggt    6660
tttgcgccat tcgatggtgt ccgggatctc gacgctctcc cttatgcgac tcctgcatta    6720
ggaagcagcc cagtagtagg ttgaggccgt tgagcaccgc cgccgcaagg aatggtgcat    6780
gcaaggagat ggcgcccaac agtccccgg ccacggggcc tgccaccata cccacgccga     6840
aacaagcgct catgagcccg aagtggcgag cccgatcttc cccatcggtg atgtcggcga    6900
tataggcgcc agcaaccgca cctgtggcgc cggtgatgcc ggccacgatg cgtccggcgt    6960
agaggatcga gatcttgtac atccctatca gtgatagaga ttgacatccc tatcagtgat    7020
agagatactg agcacatcag caggacgcac tgaccgattt cattaaagag gagaaaggta    7080
ccatgggaga aagcttgttt aagggaccac gtgattacaa cccgatatcg agcaccattt    7140
gtcatttgac gaatgaatct gatgggcaca caacatcgtt gtatggtatt ggatttggtc    7200
ccttcatcat tacaaacaag cacttgttta gaagaaataa tggaacactg ttggtccaat    7260
cactacatgg tgtattcaag gtcaagaaca ccacgacttt gcaacaacac ctcattgatg    7320
ggagggacat gataattatt cgcatgccta aggatttccc accatttcct caaaagctga    7380
aatttagaga gccacaaagg gaagagcgca tatgtcttgt gacaaccaac ttccaaacta    7440
agagcatgtc tagcatggtg tcagacacta gttgcacatt cccttcatct gatggcatat    7500
tctggaagca ttggattcaa accaaggatg ggcagtgtgg cagtccatta gtatcaacta    7560
gagatgggtt cattgttggt atacactcag catcgaattt caccaacaca acaattatt     7620
tcacaagcgt gccgaaaaac ttcatggaat tgttgacaaa tcaggaggcg cagcagtggg    7680
ttagtggttg gcgattaaat gctgactcag tattgtgggg gggccataaa gttttcatgg    7740
tgaaacctga agagcctttt cagccagtta aggaagcgac tcaactcatg aatgaattgg    7800
tgtactcgca atgataggga tccggctgct aacaaagccc gaaaggaagc tgagttggct    7860
gctgccaccg ctgagcaata actagcataa ccccttgggg cctctaaacg ggtcttgagg    7920
ggttttttgc tgaaaggagg aactatatcc ggatatcccg caagaggccc ggcagtaccg    7980
gcataaccaa gcctatgcct acagcatcca gggtgacggt gccgaggatg acgatgagcg    8040
cattgttaga tttcatacac ggtgcctgac tgcgttagca atttaactgt gataaactac    8100
cgcattaaag cttatcgatc tcgatcccgc gaaat                               8135
```

<210> SEQ ID NO 49

<211> LENGTH: 1905
<212> TYPE: DNA
<213> ORGANISM: Artificial Sequence
<220> FEATURE:
<223> OTHER INFORMATION: VIP ELP1-120

<400> SEQUENCE: 49

| | | | | | |
|---|---|---|---|---|---|
| cactctgacg | ctgttttcac | tgacaactac | actcgtctgc | gtaaacagat | ggctgttaaa | 60 |
| aagtacctga | actctatcct | gaacgtaccg | ggcgtgggtg | ttccgggcgt | gggtgttccg | 120 |
| ggtggcggtg | tgccgggcgc | aggtgttcct | ggtgtaggtg | tgccgggtgt | tggtgtgccg | 180 |
| ggtgttggtg | taccaggtgg | cggtgttccg | ggtgcaggcg | ttccgggtgg | cggtgtgccg | 240 |
| ggcgtgggtg | ttccgggcgt | gggtgttccg | ggtggcggtg | tgccgggcgc | aggtgttcct | 300 |
| ggtgtaggtg | tgccgggtgt | tggtgtgccg | ggtgttggtg | taccaggtgg | cggtgttccg | 360 |
| ggtgcaggcg | ttccgggtgg | cggtgtgccg | ggcgtgggtg | ttccgggcgt | gggtgttccg | 420 |
| ggtggcggtg | tgccgggcgc | aggtgttcct | ggtgtaggtg | tgccgggtgt | tggtgtgccg | 480 |
| ggtgttggtg | taccaggtgg | cggtgttccg | ggtgcaggcg | ttccgggtgg | cggtgtgccg | 540 |
| ggcgtgggtg | ttccgggcgt | gggtgttccg | ggtggcggtg | tgccgggcgc | aggtgttcct | 600 |
| ggtgtaggtg | tgccgggtgt | tggtgtgccg | ggtgttggtg | taccaggtgg | cggtgttccg | 660 |
| ggtgcaggcg | ttccgggtgg | cggtgtgccg | ggcgtgggtg | ttccgggcgt | gggtgttccg | 720 |
| ggtggcggtg | tgccgggcgc | aggtgttcct | ggtgtaggtg | tgccgggtgt | tggtgtgccg | 780 |
| ggtgttggtg | taccaggtgg | cggtgttccg | ggtgcaggcg | ttccgggtgg | cggtgtgccg | 840 |
| ggcgtgggtg | ttccgggcgt | gggtgttccg | ggtggcggtg | tgccgggcgc | aggtgttcct | 900 |
| ggtgtaggtg | tgccgggtgt | tggtgtgccg | ggtgttggtg | taccaggtgg | cggtgttccg | 960 |
| ggtgcaggcg | ttccgggtgg | cggtgtgccg | ggcgtgggtg | ttccgggcgt | gggtgttccg | 1020 |
| ggtggcggtg | tgccgggcgc | aggtgttcct | ggtgtaggtg | tgccgggtgt | tggtgtgccg | 1080 |
| ggtgttggtg | taccaggtgg | cggtgttccg | ggtgcaggcg | ttccgggtgg | cggtgtgccg | 1140 |
| ggcgtgggtg | ttccgggcgt | gggtgttccg | ggtggcggtg | tgccgggcgc | aggtgttcct | 1200 |
| ggtgtaggtg | tgccgggtgt | tggtgtgccg | ggtgttggtg | taccaggtgg | cggtgttccg | 1260 |
| ggtgcaggcg | ttccgggtgg | cggtgtgccg | ggcgtgggtg | ttccgggcgt | gggtgttccg | 1320 |
| ggtggcggtg | tgccgggcgc | aggtgttcct | ggtgtaggtg | tgccgggtgt | tggtgtgccg | 1380 |
| ggtgttggtg | taccaggtgg | cggtgttccg | ggtgcaggcg | ttccgggtgg | cggtgtgccg | 1440 |
| ggcgtgggtg | ttccgggcgt | gggtgttccg | ggtggcggtg | tgccgggcgc | aggtgttcct | 1500 |
| ggtgtaggtg | tgccgggtgt | tggtgtgccg | ggtgttggtg | taccaggtgg | cggtgttccg | 1560 |
| ggtgcaggcg | ttccgggtgg | cggtgtgccg | ggcgtgggtg | ttccgggcgt | gggtgttccg | 1620 |
| ggtggcggtg | tgccgggcgc | aggtgttcct | ggtgtaggtg | tgccgggtgt | tggtgtgccg | 1680 |
| ggtgttggtg | taccaggtgg | cggtgttccg | ggtgcaggcg | ttccgggtgg | cggtgtgccg | 1740 |
| ggcgtgggtg | ttccgggcgt | gggtgttccg | ggtggcggtg | tgccgggcgc | aggtgttcct | 1800 |
| ggtgtaggtg | tgccgggtgt | tggtgtgccg | ggtgttggtg | taccaggtgg | cggtgttccg | 1860 |
| ggtgcaggcg | ttccgggtgg | cggtgtgccg | ggctggccgt | gataa | | 1905 |

<210> SEQ ID NO 50
<211> LENGTH: 633
<212> TYPE: PRT
<213> ORGANISM: Artificial Sequence
<220> FEATURE:
<223> OTHER INFORMATION: VIP ELP1-120

<400> SEQUENCE: 50

```
His Ser Asp Ala Val Phe Thr Asp Asn Tyr Thr Arg Leu Arg Lys Gln
  1               5                  10                  15

Met Ala Val Lys Lys Tyr Leu Asn Ser Ile Leu Asn Val Pro Gly Val
             20                  25                  30

Gly Val Pro Gly Val Gly Val Pro Gly Gly Gly Val Pro Gly Ala Gly
             35                  40                  45

Val Pro Gly Val Gly Val Pro Gly Val Gly Val Pro Gly Val Gly Val
     50                  55                  60

Pro Gly Gly Gly Val Pro Gly Ala Gly Val Pro Gly Gly Gly Val Pro
 65                  70                  75                  80

Gly Val Gly Val Pro Gly Val Gly Val Pro Gly Gly Gly Val Pro Gly
             85                  90                  95

Ala Gly Val Pro Gly Val Gly Val Pro Gly Val Gly Val Pro Gly Val
            100                 105                 110

Gly Val Pro Gly Gly Gly Val Pro Gly Ala Gly Val Pro Gly Gly Gly
            115                 120                 125

Val Pro Gly Val Gly Val Pro Gly Val Gly Val Pro Gly Gly Gly Val
    130                 135                 140

Pro Gly Ala Gly Val Pro Gly Val Gly Val Pro Gly Val Gly Val Pro
145                 150                 155                 160

Gly Val Gly Val Pro Gly Gly Gly Val Pro Gly Ala Gly Val Pro Gly
            165                 170                 175

Gly Gly Val Pro Gly Val Gly Val Pro Gly Val Gly Val Pro Gly Gly
            180                 185                 190

Gly Val Pro Gly Ala Gly Val Pro Gly Val Gly Val Pro Gly Val Gly
            195                 200                 205

Val Pro Gly Val Gly Val Pro Gly Gly Gly Val Pro Gly Ala Gly Val
    210                 215                 220

Pro Gly Gly Gly Val Pro Gly Val Gly Val Pro Gly Val Gly Val Pro
225                 230                 235                 240

Gly Gly Gly Val Pro Gly Ala Gly Val Pro Gly Val Gly Val Pro Gly
            245                 250                 255

Val Gly Val Pro Gly Val Gly Val Pro Gly Gly Gly Val Pro Gly Ala
            260                 265                 270

Gly Val Pro Gly Gly Gly Val Pro Gly Val Gly Val Pro Gly Val Gly
            275                 280                 285

Val Pro Gly Gly Gly Val Pro Gly Ala Gly Val Pro Gly Val Gly Val
    290                 295                 300

Pro Gly Val Gly Val Pro Gly Val Gly Val Pro Gly Gly Gly Val Pro
305                 310                 315                 320

Gly Ala Gly Val Pro Gly Gly Gly Val Pro Gly Val Gly Val Pro Gly
            325                 330                 335

Val Gly Val Pro Gly Gly Gly Val Pro Gly Ala Gly Val Pro Gly Val
            340                 345                 350

Gly Val Pro Gly Val Gly Val Pro Gly Val Gly Val Pro Gly Gly Gly
            355                 360                 365

Val Pro Gly Ala Gly Val Pro Gly Gly Gly Val Pro Gly Val Gly Val
            370                 375                 380

Pro Gly Val Gly Val Pro Gly Gly Gly Val Pro Gly Ala Gly Val Pro
385                 390                 395                 400

Gly Val Gly Val Pro Gly Val Gly Val Pro Gly Val Gly Val Pro Gly
```

-continued

```
                405                  410                 415
Gly Gly Val Pro Gly Ala Gly Val Pro Gly Gly Gly Val Pro Gly Val
            420                 425                 430

Gly Val Pro Gly Val Gly Val Pro Gly Gly Gly Val Pro Gly Ala Gly
        435                 440                 445

Val Pro Gly Val Gly Val Pro Gly Val Gly Val Pro Gly Val Gly Val
    450                 455                 460

Pro Gly Gly Gly Val Pro Gly Ala Gly Val Pro Gly Gly Gly Val Pro
465                 470                 475                 480

Gly Val Gly Val Pro Gly Val Gly Val Pro Gly Gly Gly Val Pro Gly
            485                 490                 495

Ala Gly Val Pro Gly Val Gly Val Pro Gly Val Gly Val Pro Gly Val
            500                 505                 510

Gly Val Pro Gly Gly Gly Val Pro Gly Ala Gly Val Pro Gly Gly Gly
        515                 520                 525

Val Pro Gly Val Gly Val Pro Gly Val Gly Val Pro Gly Gly Gly Val
    530                 535                 540

Pro Gly Ala Gly Val Pro Gly Val Gly Val Pro Gly Val Gly Val Pro
545                 550                 555                 560

Gly Val Gly Val Pro Gly Gly Gly Val Pro Gly Ala Gly Val Pro Gly
            565                 570                 575

Gly Gly Val Pro Gly Val Gly Val Pro Gly Val Gly Val Pro Gly Gly
        580                 585                 590

Gly Val Pro Gly Ala Gly Val Pro Gly Val Gly Val Pro Gly Val Gly
        595                 600                 605

Val Pro Gly Val Gly Val Pro Gly Gly Gly Val Pro Gly Ala Gly Val
    610                 615                 620

Pro Gly Gly Gly Val Pro Gly Trp Pro
625                 630
```